(12) United States Patent
Thum et al.

(10) Patent No.: US 8,691,783 B2
(45) Date of Patent: Apr. 8, 2014

(54) MICRORNA-24

(75) Inventors: Thomas Thum, Hannover (DE); Jan Fiedler, Hannover (DE)

(73) Assignee: Julius-Maximilians-Universitaet Wuerzburg, Wuerzburg (DE)

(*) Notice: Subject to any disclaimer, the term of this patent is extended or adjusted under 35 U.S.C. 154(b) by 0 days.

(21) Appl. No.: 13/384,228

(22) PCT Filed: Jul. 16, 2010

(86) PCT No.: PCT/EP2010/004360
§ 371 (c)(1),
(2), (4) Date: Mar. 27, 2012

(87) PCT Pub. No.: WO2011/006669
PCT Pub. Date: Jan. 20, 2011

(65) Prior Publication Data
US 2012/0180147 A1    Jul. 12, 2012

(30) Foreign Application Priority Data
Jul. 16, 2009   (EP) .................................... 09075314

(51) Int. Cl.
*A61K 48/00*   (2006.01)
*C12N 15/11*   (2006.01)
*C07H 21/02*   (2006.01)
*C07H 21/04*   (2006.01)

(52) U.S. Cl.
USPC ...................................... 514/44 A; 536/24.5

(58) Field of Classification Search
USPC .......................................... 514/44; 536/24.5
See application file for complete search history.

(56) References Cited

FOREIGN PATENT DOCUMENTS

WO    WO 2008/151631 A2    12/2008

OTHER PUBLICATIONS

Fiedler et al. (Circulation, 2011, vol. 124:720-730).*
Bonauer et at, "MicroRNA-92a Controls Angiogenesis and Functional Recovery of Ischemic Tissues in Mice", Science, 2009, vol. 324, No. 5935, pp. 1710-1713.
Carmona etal., "Role of the small GTPase Rap1 for integrin activity regulation in endothelial cells and angiogenesis", Blood, 2009, vol. 113, No. 2, pp. 488-497.

(Continued)

Primary Examiner — Terra Cotta Gibbs
(74) Attorney, Agent, or Firm — Saliwanchik, Lloyd & Eisenschenk

(57) ABSTRACT

The present invention relates to a modulator, in particular an inhibitor, of microRNA-24 (miR-24) and to direct and indirect miR-24 targets for use in a method of treatment and/or prevention of ischemia, in a method of prevention of endothelial apoptosis or in a method of induction of angiogenesis. The present invention further relates to a precursor of miR-24 and to siRNAs or shRNAs against direct or indirect miR-24 targets for use in a method of treatment of angiogenesis associated with cancer. The present invention also relates to an in vitro method for diagnosing ischemia or prevalence or disposition for ischemia, and to a method for identifying a modulator of miR-24 and/or direct or indirect miR-24 targets. In addition, the present invention relates to pharmaceutical compositions or kits comprising any of the above agents, to endothelial cells devoid of expressing functional miR-24, and to a non-human, transgenic animal comprising these endothelial cells.

4 Claims, 26 Drawing Sheets

(56) References Cited

OTHER PUBLICATIONS

Chen et al., "Resveratrol protects cardiomyocytes from hypoxia-induced apoptosis through the SIRT1-Fox01 pathway", *Biochemical and Biophysical Research Communications*, 2009, vol. 378, No. 3, pp. 389-393.

Cheng et al., "Antisense inhibition of human miRNAs and indications for an involvement of miRNA in cell growth and apoptosis", *Nucleic Acids Research*, 2005, vol. 33, No. 4, pp. 1290-1297.

Hoang et al., "Netrin-4 enhances angiogenesis and neurologic outcome after cerebral ischemia", *Journal of Cerebral Blood Flow and Metabolism*, 2009, vol. 29, No. 2, pp. 385-397.

Lal et al., "p16$^{INK4a}$ Translation Suppressed by miR-24", *PLoS one*, 2008, vol. 3, No. 3, pp. E1684.

Potente et al., "SIRT1 controls endothelial angiogenic functions during vascular growth", *Genes and Development*, 2007, vol. 21, No. 20, pp. 2644-2658.

\* cited by examiner

SEQUENCE LISTING

```
<160> NUMBER OF SEQ ID NOS: 26

<210> SEQ ID NO 1
<211> LENGTH: 22
<212> TYPE: RNA
<213> ORGANISM: Homo sapiens

<400> SEQUENCE: 1
uggcucaguu cagcaggaac ag                                               22

<210> SEQ ID NO 2
<211> LENGTH: 22
<212> TYPE: RNA
<213> ORGANISM: Mus musculus

<400> SEQUENCE: 2
uggcucaguu cagcaggaac ag                                               22

<210> SEQ ID NO 3
<211> LENGTH: 22
<212> TYPE: DNA
<213> ORGANISM: Artificial sequence
<220> FEATURE:
<223> OTHER INFORMATION: antagomir-24: 5'-CTGTTCCTGCTGAACTGAGCCA-chol-3'
<220> FEATURE:
<221> NAME/KEY: misc_feature
<222> LOCATION: (22)..(22)
<223> OTHER INFORMATION: chol-3': at the 3'-end of antagomir

<400> SEQUENCE: 3
ctgttcctgc tgaactgagc ca                                               22

<210> SEQ ID NO 4
<211> LENGTH: 23
<212> TYPE: RNA
<213> ORGANISM: Artificial sequence
<220> FEATURE:
<223> OTHER INFORMATION: scrambled antagomir:
      5'-ACAAACACCAUUGUCACACUCCA-chol-3'
<220> FEATURE:
<221> NAME/KEY: misc_feature
<222> LOCATION: (23)..(23)
<223> OTHER INFORMATION: chol-3': at the 3'-end of scrambled antagomir

<400> SEQUENCE: 4
acaaacacca uugucacacu cca                                              23

<210> SEQ ID NO 5
<211> LENGTH: 28
<212> TYPE: DNA
```

```
<213> ORGANISM: Artificial sequence
<220> FEATURE:
<223> OTHER INFORMATION: GATA2 wild-type sequence

<400> SEQUENCE: 5
caggctgggc tgagccaaag ccagagtg                                              28

<210> SEQ ID NO 6
<211> LENGTH: 28
<212> TYPE: DNA
<213> ORGANISM: Artificial sequence
<220> FEATURE:
<223> OTHER INFORMATION: GATA2 mutant sequence

<400> SEQUENCE: 6
caggctgggc tggtacaaag ccagagtg                                              28

<210> SEQ ID NO 7
<211> LENGTH: 28
<212> TYPE: DNA
<213> ORGANISM: Artificial sequence
<220> FEATURE:
<223> OTHER INFORMATION: PAK4 wild-type sequence

<400> SEQUENCE: 7
cctctccccc tgagccattg gggggggtc                                             28

<210> SEQ ID NO 8
<211> LENGTH: 28
<212> TYPE: DNA
<213> ORGANISM: Artificial sequence
<220> FEATURE:
<223> OTHER INFORMATION: PAK4 mutant sequence

<400> SEQUENCE: 8
cctctccccc tgctccattg gggggggtc                                             28

<210> SEQ ID NO 9
<211> LENGTH: 20
<212> TYPE: DNA
<213> ORGANISM: Artificial sequence
<220> FEATURE:
<223> OTHER INFORMATION: primer used for mRNA RT-PCR

<400> SEQUENCE: 9
ttgaccctaa ccaaggatgc                                                       20

<210> SEQ ID NO 10
<211> LENGTH: 20
<212> TYPE: DNA
<213> ORGANISM: Artificial sequence
<220> FEATURE:
<223> OTHER INFORMATION: primer used for mRNA RT-PCR

<400> SEQUENCE: 10
caccccttct gcgttgtatt                                                       20

<210> SEQ ID NO 11
<211> LENGTH: 20
<212> TYPE: DNA
<213> ORGANISM: Artificial sequence
<220> FEATURE:
<223> OTHER INFORMATION: primer used for mRNA RT-PCR

<400> SEQUENCE: 11
aactcccatt cctccacctt                                                       20
```

```
<210> SEQ ID NO 12
<211> LENGTH: 20
<212> TYPE: DNA
<213> ORGANISM: Artificial sequence
<220> FEATURE:
<223> OTHER INFORMATION: primer used for mRNA RT-PCR

<400> SEQUENCE: 12
gagggcctct ctcttgctct                                               20

<210> SEQ ID NO 13
<211> LENGTH: 21
<212> TYPE: DNA
<213> ORGANISM: Artificial sequence
<220> FEATURE:
<223> OTHER INFORMATION: oligonucleotide used for in situ hybridization

<400> SEQUENCE: 13
ggaaatccct ggcaatgtga t                                             21

<210> SEQ ID NO 14
<211> LENGTH: 21
<212> TYPE: DNA
<213> ORGANISM: Artificial sequence
<220> FEATURE:
<223> OTHER INFORMATION: oligonucleotide used for in situ hybridization

<400> SEQUENCE: 14
ggtaatccct ggcaatgtga t                                             21

<210> SEQ ID NO 15
<211> LENGTH: 21
<212> TYPE: DNA
<213> ORGANISM: Artificial sequence
<220> FEATURE:
<223> OTHER INFORMATION: oligonucleotide used for in situ hybridization

<400> SEQUENCE: 15
gcggaactta gccactgtga a                                             21

<210> SEQ ID NO 16
<211> LENGTH: 21
<212> TYPE: DNA
<213> ORGANISM: Artificial sequence
<220> FEATURE:
<223> OTHER INFORMATION: oligonucleotide used for in situ hybridization

<400> SEQUENCE: 16
gcagaactta gccactgtga a                                             21

<210> SEQ ID NO 17
<211> LENGTH: 20
<212> TYPE: DNA
<213> ORGANISM: Artificial sequence
<220> FEATURE:
<223> OTHER INFORMATION: primer used for ChIP-PCR

<400> SEQUENCE: 17
tctcaggttt tggagggaga                                               20

<210> SEQ ID NO 18
<211> LENGTH: 20
<212> TYPE: DNA
<213> ORGANISM: Artificial sequence
<220> FEATURE:
<223> OTHER INFORMATION: primer used for ChIP-PCR
```

-continued

```
<400> SEQUENCE: 18
ggccgagact gacactcaat                                                 20

<210> SEQ ID NO 19
<211> LENGTH: 20
<212> TYPE: DNA
<213> ORGANISM: Artificial sequence
<220> FEATURE:
<223> OTHER INFORMATION: primer used for ChIP-PCR

<400> SEQUENCE: 19
caagtgatat gccagggtca                                                 20

<210> SEQ ID NO 20
<211> LENGTH: 20
<212> TYPE: DNA
<213> ORGANISM: Artificial sequence
<220> FEATURE:
<223> OTHER INFORMATION: primer used for ChIP-PCR

<400> SEQUENCE: 20
tggttgtttt gcatgaggac                                                 20

<210> SEQ ID NO 21
<211> LENGTH: 20
<212> TYPE: DNA
<213> ORGANISM: Artificial sequence
<220> FEATURE:
<223> OTHER INFORMATION: primer used for ChIP-PCR

<400> SEQUENCE: 21
catcaccaga cccagacaga                                                 20

<210> SEQ ID NO 22
<211> LENGTH: 20
<212> TYPE: DNA
<213> ORGANISM: Artificial sequence
<220> FEATURE:
<223> OTHER INFORMATION: primer used for ChIP-PCR

<400> SEQUENCE: 22
aaggccgact ttaagggaag                                                 20

<210> SEQ ID NO 23
<211> LENGTH: 23
<212> TYPE: DNA
<213> ORGANISM: Artificial sequence
<220> FEATURE:
<223> OTHER INFORMATION: primer used for ChIP-PCR

<400> SEQUENCE: 23
gagccagtta ttcagcaaag aaa                                             23

<210> SEQ ID NO 24
<211> LENGTH: 20
<212> TYPE: DNA
<213> ORGANISM: Artificial sequence
<220> FEATURE:
<223> OTHER INFORMATION: primer used for ChIP-PCR

<400> SEQUENCE: 24
atgcagaggc catgctaatc                                                 20

<210> SEQ ID NO 25
<211> LENGTH: 20
<212> TYPE: DNA
```

```
<213> ORGANISM: Artificial sequence
<220> FEATURE:
<223> OTHER INFORMATION: primer used for ChIP-PCR

<400> SEQUENCE: 25
ggagtcacag tgtgccagaa                                             20

<210> SEQ ID NO 26
<211> LENGTH: 20
<212> TYPE: DNA
<213> ORGANISM: Artificial sequence
<220> FEATURE:
<223> OTHER INFORMATION: primer used for ChIP-PCR

<400> SEQUENCE: 26
ccttcctttc tagcgtgagc                                             20
```

MICRORNA-24

CROSS REFERENCE TO A RELATED APPLICATION

This application is a National Stage Application of International Application Number PCT/EP2010/004360, filed Jul. 16, 2010; which claims priority to European Patent Application No. 09075314.6, filed Jul. 16, 2009; all of which are incorporated herein by reference in their entirety.

The Sequence Listing for this application is labeled "SeqList-27Aug13_ST25.txt" which was created on Aug. 27, 2013 and is 6 KB. The entire content of the sequence listing is incorporated herein by reference in its entirety.

FIELD OF THE INVENTION

The present invention relates to a modulator, in particular an inhibitor, of microRNA-24 (miR-24) and to direct and indirect miR-24 targets for use in a method of treatment and/or prevention of ischemia, in a method of prevention of endothelial apoptosis or in a method of induction of angiogenesis. The present invention further relates to a precursor of miR-24 and to siRNAs or shRNAs against direct or indirect miR-24 targets for use in a method of treatment of angiogenesis associated with cancer. The present invention also relates to an in vitro method for diagnosing ischemia or prevalence or disposition for ischemia, and to a method for identifying a modulator of miR-24 and/or direct or indirect miR-24 targets. In addition, the present invention relates to pharmaceutical compositions or kits comprising any of the above agents, to endothelial cells devoid of expressing functional miR-24, and to a non-human, transgenic animal comprising these endothelial cells.

BACKGROUND OF THE INVENTION

MicroRNAs (miRNAs) are endogenous small non-coding single stranded RNAs that control diverse biological processes and major signaling pathways, like developmental timing, hematopoietic cell differentiation, apoptosis, cell proliferation, and organ development. They regulate the expression of complementary target mRNAs by post-transcriptional gene silencing, which leads to mRNA cleavage or translational repression. With more than 200 members per species in higher eukaryotes, miRNAs are one of the largest gene families accounting for about 1% of the genome (Bartel, 2004). More than one third of all human genes are targeted by miRNAs. MiRNAs and their targets seem to form complex regulatory networks. For example, a single miRNA regulates many different mRNA targets, and several different miRNAs control a single mRNA target. Consequently, the unique combination of miRNAs that are expressed in each cell type might affect the utilization of thousands of mRNAs.

MiRNAs were recently implicated in the regulation of diverse cardiac functions in a series of genetic studies (Care et al., 2007). Myocardial infarction results in hypoxia of cardiac tissue that triggers an array of pathophysiological effects including cardiomyocyte apoptosis and impairment of vascularization. Studies have shown miRNAs to be important for regulation of endothelial function, especially angiogenesis (Wang et al., 2008). Although these studies help to delineate the role of miRNA in heart physiology, growth and morphogenesis, molecular mechanisms for miRNAs in cardiac disease pathways are poorly understood. MiR-24 is expressed in a variety of organs (FIG. 6), but its role in the cardiovascular system is unclear. Therefore, the therapeutic potential of specific miRNAs and their antagonists in cardiac diseases remains to be established.

Myocardial infarction and cardiac dysfunction represent a critical health burden worldwide (http://www.who.int/whosis/whostat/2009/en/index.html, WHO, 2009). Due to the increased life expectancy, incidence and prevalence of cardiovascular diseases will rise. Cardiac ischemia triggers left ventricular remodeling and development of heart failure, and the prognosis of heart failure is as bad as for certain malignant tumors (Hill et al., 2008). A central issue of ventricular remodeling after myocardial infarction is an insufficient angiogenesis. Therapies improving neovascularization after myocardial infarction favorably affect cardiac outcome, however, such approaches are scarce and mechanistically not well understood.

Therefore, therapies for the improvement in particular of cardiac healing processes post cardiovascular diseases have to be developed.

The solution to this problem is achieved by providing the embodiments characterized by the claims, and described further below.

SUMMARY OF THE INVENTION

A first aspect of the present invention relates to a modulator, in particular an inhibitor, of microRNA-24 (miR-24) for use in a method of treatment and/or prevention of ischemia, in a method of prevention of endothelial apoptosis or in a method of induction of angiogenesis.

In one embodiment, the ischemia is associated with at least one of the group of acute and/or chronic myocardial infarction, chronic heart failure, peripheral vascular occlusive disease, liver and/or kidney ischemia, stroke, bowel ischemia and chronic ulcers of the skin and/or the mucosa.

In one embodiment, the inhibitor is an antagomir or an antisense oligonucleotide.

In one embodiment, the antagomir or the antisense oligonucleotide is essentially complementary to SEQ ID NO: 1. In a preferred embodiment, the antagomir has a sequence represented by SEQ ID NO: 3.

A further aspect of the present invention relates to a direct or indirect microRNA-24 (miR-24) target for use in a method of treatment and/or prevention of ischemia, in a method of prevention of endothelial apoptosis or in a method of induction of angiogenesis.

Preferably, the direct or indirect microRNA-24 (miR-24) target is used by activating/increasing its expression and/or activity in cells, in particular endothelial cells.

In one embodiment, the ischemia is associated with at least one of the group of acute and/or chronic myocardial infarction, chronic heart failure, peripheral vascular occlusive disease, liver and/or kidney ischemia, stroke, bowel ischemia and chronic ulcers of the skin and/or the mucosa.

In one embodiment, the direct target is selected from the group of GATA2, PAK4, RASA1, CDKN1B, AMOTL2, H2AFX, RAP1B, AXL, S1PR1, MAGI1, TFPI, ANGPT4 and BMPR2, preferably from the group of GATA2, PAK4, RASA1, AMOTL2, S1PR1, ANGPT4 and BMPR2, even more preferably from the group of GATA2, PAK4 and RASA1.

In one embodiment, the indirect target is selected from the group of phosphorylated BAD, heme oxygenase 1 (HO-1 or HMOX-1), sirt1, bambi, esm1 and ntn4.

A further aspect of the present invention relates to a precursor of miR-24 (pre-miR-24) for use in a method of treatment of angiogenesis associated with cancer.

A further aspect of the present invention relates to a siRNA or shRNA against a direct or indirect miR-24 target for use in a method of treatment of angiogenesis associated with cancer, wherein the direct miR-24 target is preferably selected from the group of GATA2, PAK4, RASA1, AMOTL2, S1PR1, ANGPT4 and BMPR2. Preferably, the indirect target is selected from the group of heme oxygenase 1 (HO-1 or HMOX-1), sirt1, bambi, esm1 and ntn4.

A further aspect of the present invention relates to an in vitro method for diagnosing ischemia or prevalence or disposition for ischemia, comprising the steps of:
a) providing a test sample of a subject comprising endothelial cells;
b) identifying the amount of miR-24 and/or of at least one direct or indirect miR-24 target in the test sample;
c) comparing the amount of miR-24 and/or of the at least one direct or indirect miR-24 target in the test sample with a control sample;
wherein an up-regulation of miR-24 and/or a down-regulation of the at least one direct or indirect miR-24 target in the test sample, in comparison to the control sample, indicates ischemia or prevalence or disposition for ischemia.

A further aspect of the present invention relates to a method for identifying a modulator of miR-24 and/or of a direct or indirect miR-24 target comprising the steps of:
a) providing a cell culture expressing miR-24 and/or a direct or indirect miR-24 target;
b) contacting a candidate substance with the cell culture;
c) assessing the expression and/or activity of miR-24 and/or of the direct or indirect miR-24 target;
d) comparing the expression and/or activity of miR-24 and/or of the direct or indirect miR-24 target of step c) with the expression and/or activity in the absence of the candidate compound,
wherein a difference in the expression and/or activity of miR-24 and/or of the direct or indirect miR-24 target qualifies the candidate substance as a modulator of miR-24 and/or of the direct or indirect miR-24 target.

A further aspect of the present invention relates to a pharmaceutical composition or kit comprising a modulator, in particular an inhibitor, of microRNA-24 (miR-24) as defined above, preferably an antagomir and/or an antisense oligonucleotide which is essentially complementary to SEQ ID NO: 1, more preferably an antagomir having a sequence represented by SEQ ID NO: 3.

In one embodiment, the pharmaceutical composition or kit as defined above, further comprises at least one direct or indirect miR-24 target as defined above.

A further aspect of the present invention relates to a pharmaceutical composition or kit comprising at least one direct or indirect miR-24 target as defined above.

A further aspect of the present invention relates to a pharmaceutical composition or kit comprising a precursor of miR-24 (pre-miR-24) as defined above and/or a siRNA or shRNA against a direct or indirect miR-24 target as defined above.

A further aspect of the present invention relates to an endothelial cell devoid of expressing functional miR-24.

A further aspect of the present invention relates to a non-human, transgenic animal comprising cells devoid of expressing functional miR-24.

In a further aspect the present invention relates to a method for treating ischemia in a subject in need thereof, comprising the steps of:
a) identifying a subject suffering from ischemia;
b) inhibiting the expression and/or activity of miR-24 and/or activating/increasing the expression and/or activity of at least one direct or indirect miR-24 target as defined above in cells, in particular endothelial cells, of the subject.

In a still further aspect, the invention relates to a method for preventing ischemia in a subject which is at risk of developing ischemia, comprising the steps of:
a) identifying a subject which is at risk of developing ischemia;
b) inhibiting the expression and/or activity of miR-24 and/or activating/increasing the expression and/or activity of at least one direct or indirect miR-24 target as defined above in cells, in particular endothelial cells, of the subject.

In another aspect the invention relates to a method for preventing endothelial apoptosis in a subject in need thereof, comprising the step of inhibiting the expression and/or activity of miR-24 and/or activating/increasing the expression and/or activity of at least one direct or indirect miR-24 target as defined above in endothelial cells of the subject.

In a further aspect, the present invention relates to a method for inducing angiogenesis in a subject in need thereof, comprising the step of inhibiting the expression and/or activity of miR-24 and/or activating/increasing the expression and/or activity of at least one direct or indirect miR-24 target as defined above in cells, in particular endothelial cells, of the subject.

In a further aspect, the present invention relates to a method for treating angiogenesis associated with cancer in a subject in need thereof, comprising the step of activating/increasing the expression and/or activity of miR-24 (e.g. by applying pre-miR-24) and/or inhibiting the expression and/or activity of at least one direct or indirect miR-24 target as defined above in cancer cells of the subject.

Another aspect of the present invention relates to the use of
 a modulator, in particular an inhibitor, of microRNA-24 (miR-24) as defined above and/or
 a direct or indirect microRNA-24 (miR-24) target as defined above
for the manufacture of a medicament for the treatment and/or prevention of ischemia, of a medicament for the prevention of endothelial apoptosis or of a medicament for the induction of angiogenesis.

A further aspect of the present invention relates to the use of
 a precursor of microRNA-24 (pre-miR-24) and/or
 a siRNA or shRNA against a direct or indirect miR-24 target as defined above
for the manufacture of a medicament for the treatment of angiogenesis associated with cancer.

The invention will be more apparent from the disclosure of the following description together with the figures and sequence listing.

SEQUENCE LISTING

Figure 1:
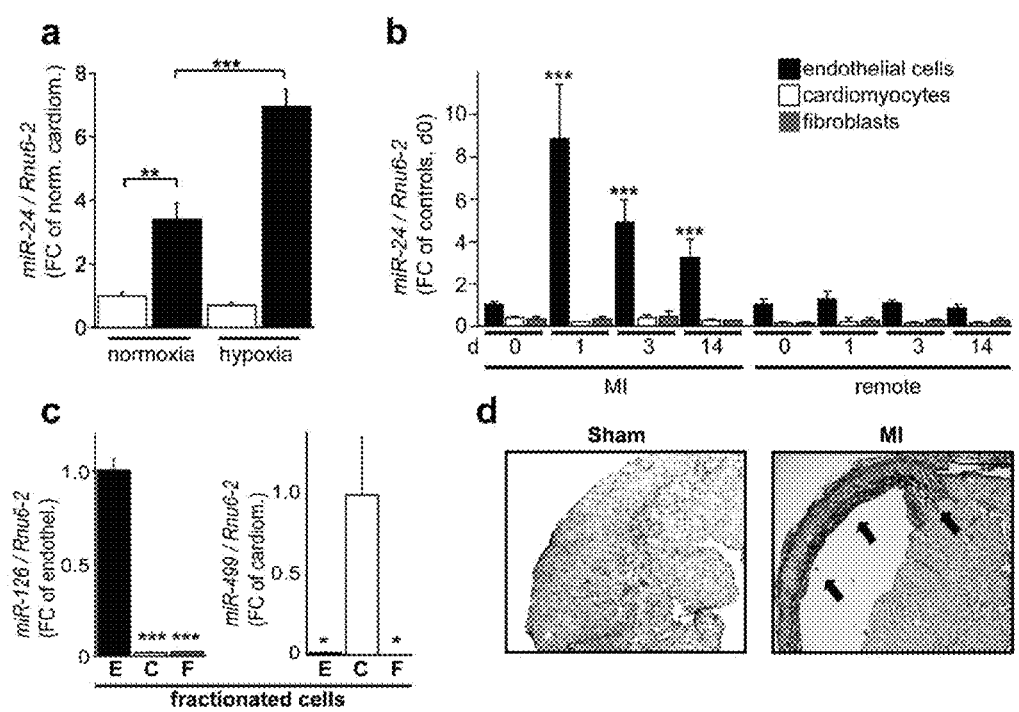
FIG. 1 shows selective miR-24 upregulation in endothelial cells after myocardial infarction and hypoxia. (a) Expression of miR-24/RNU6-2 in human umbilical vein endothelial cells (HUVEC) and rat neonatal cardiomyocytes 24 h after normoxic (21% $O_2$) or hypoxic conditions (1% $O_2$). (b) Expression of miR-24 relative to Rnu6-2 in fractionated endothelial cells (magnetic affinity cell sorted CD146$^+$ cells), cardiac fibroblasts and cardiomyocytes of the periinfarct or remote region 0 d, 1 d, 3 d or 14 d after myocardial infarction (MI) of mice. (c) Expression of cell-type specific miRNAs in fractionated cardiac endothelial cells (E), cardiomyocytes (C) and fibroblasts (F). (d) In situ hybridization of miR-24 in infarcted (MI) and non-infarcted (Sham) mouse myocardium. Black arrows point on regions with intense hybridization signals. n=3-7 per experiments or animals per group. Data are mean and s.e.m.; *P, 0.05, P, 0.01, *P, 0.005. Scale bar, 1.0 mm.

SEQ ID NO: 1 represents the sequence of human miR-24.
SEQ ID NO: 2 represents the sequence of murine miR-24.
SEQ ID NO: 3 represents the sequence of antagomir-24.
SEQ ID NO: 4 represents the sequence of a scrambled antagomir.

DETAILED DESCRIPTION OF THE INVENTION

A first aspect of the present invention relates to a modulator, in particular an inhibitor, of microRNA-24 (miR-24) for use in a method of treatment and/or prevention of ischemia, in a method of prevention of endothelial apoptosis or in a method of induction of angiogenesis.

The term "microRNA-24" or "miRNA-24" as used herein refers to a family of small non-coding miRNA encoded by at least two distinct genes, MIR-24-1 and -2. The full-length miR-24-1 precursor is processed into two mature miRNAs, miR189 and miR-24 (SEQ ID NO: 1). Van Rooij et al. (2006) identified miR-24 among a group of miRNAs upregulated in two independent mouse models of cardiac hypertrophy. Northern blot analysis showed increased expression of miR-24 in idiopathic end-stage failing human hearts. Overexpression of miR-24 in cultured rat cardiomyocytes resulted in hypertrophic growth, and cardiac overexpression of miR-24 in transgenic mice was embryonic lethal. In contrast to the present invention, van Rooij did not report abnormal vessel architecture by manipulation of miR-24 expression. Wang et al. (2008) found that miR-24-1 regulated erythroid differentiation in erythroleukemic K562 cells and in CD34-positive human cord blood hematopoietic progenitor cells (HPCs) by downregulating expression of activin receptor ACVR1B.

The term "modulator, in particular inhibitor, of microRNA-24", also called miR-24 antagonist, as used herein refers to a substance or an effect that reduces or blocks activity of miRNA-24 on the DNA level, e.g. by modifying genetic translation; RNA level, e.g. by complementary oligonucleotides; and/or during RNA maturation, e.g. by splice modification. The inhibitor can act directly on miR-24 or indirectly via further compounds or effects within a signal pathway. Inhibitors of miR-24 can be naturally occurring, genetically modified or synthetic inhibitors, like morpholinos.

MiRNA modulators, in particular inhibitors, such as miRNA-mimetics, miRNA antagonists, e.g. antagomirs, or miRNA sponges provide effective tools and therapeutically relevant approaches to treat diseases. Delivering miRNA-mimics in disease states where specific miRNAs are repressed may improve or attenuate disease. In other diseases miRNAs get strongly upregulated and the goal in that case may be to lower their expression in selected cells by complementary RNA sequences. The synthetic reverse complement oligonucleotide approach can theoretically act at different levels to affect miRNA levels: (a) by binding to the mature miRNA within the RISC and acting as a competitive inhibitor; (b) by binding to the pre-miRNA and preventing its processing or entry into the RISC; (3) by interfering with the processing or export of the pre- or pri-miRNA from the nucleus.

Antagomirs are a novel class of chemically engineered cholesterol-conjugated single-strand RNA analogues that are efficient and specific silencers of endogenous microRNAs in vitro and in vivo. Inhibition of miRNAs can also be achieved with antisense 2'-O-methyl (2'-OMe) oligoribonucleotides or by use of lentivirally or adenovirally expressed antagomirs. Furthermore, MOE (2'-O-methoxyethyl phosphorothioate) or LNA (locked nucleic acid (LNA) phosphorothioate chemistry)—modification of single-stranded RNA analogues can be used to inhibit miRNA activity.

In addition, endogenous miRNAs can be silenced by the use of miRNA sponges. In that case a single species of RNA is constructed, that contains multiple, tandem-binding sites for a miRNA seed family of interest. As various members of a miRNA seed family are targeted, the potential advantage of this approach is to more effectively influence disease pathways commonly regulated by this family of miRNAs. In principle it is possible to interfere with miRNA function by scavenging away the miRNA and thereby preventing it from binding its mRNA targets.

The binding of a miRNA with a specific mRNA target can also be prevented using an oligonucleotide with perfect complementary to the miRNA target sequence in the 3'-UTR of the mRNA, which thereby masks the binding site and prevents association with the miRNA. A further approach to inhibit miRNA function can be achieved by "erasers," in which expression of a tandem repeat of a sequence perfectly complementary to the target miRNA inhibits the endogenous miRNA function. Finally, substances, molecules, drugs can be used to inhibit miRNA expression and biogenesis.

By delivering single-stranded oligonucleotides equivalent of the mature miRNA, an increase in the effective concentration of a reduced miRNA can be achieved through the use of synthetic RNA duplexes in which one strand is identical to the native miRNA. In this case, short double-stranded oligonucleotides are designed in which one strand is the mature miRNA sequence (guide strand) and a complementary or partially complementary stand is complexed with the mature miRNA sequence (passenger strand). Overexpression of miRNAs can in particular be achieved by local or systemic application of miRNA-precursor molecules/mRNA mimics or by viral overexpression of miRNAs by use of viral vectors. Finally, substances, molecules, drugs can be used to increase miRNA expression and biogenesis.

The term "ischemia" as used herein refers to a restriction or insufficiency in blood supply and/or flow to at least a part of the body. This restriction results in a lack or shortage of proper oxygen, like hypoxia, and nutrients, leading to tissue damage or dysfunction. Ischemia is caused by constriction or blockage of the supplying blood vessels. Ischemia of heart muscle produces angina pectoris. Ischemia may be caused by blood clots, congenital heart defects, head injury, stroke, hypoglycemia, tachycardia, atherosclerosis, hypotension, embolism, like thromboembolism, blood vessel constriction and outside compression of a blood vessel, e.g. by a tumor or in the case of the superior mesenteric artery syndrome, sickle cell, g-forces, which force the blood fluid to the body's extremities, like in acrobatics and military flying, localized extreme cold, such as by frostbite or improper cold compression therapy as well as other circumstances and conditions. The term "ischemia" comprises all types of ischemia independent of the pathomechanism, e.g. cardiac ischemia, bowel ischemia, ischemic colitis, mesenteric ischemia, cutaneous ischemia, and cerebral ischemia.

"Endothelial apoptosis" is observed in various physiological and pathological conditions such as wound healing, scar formation, atherosclerosis, and diabetic eye disease in the adult, as well as in developing capillaries during embryogenesis. It is also known to have an important role in angiogenesis.

The term "angiogenesis" as used herein refers to a physiological process involving the growth of new blood vessels from pre-existing vessels. The term "angiogenesis" comprises vasculogenesis as spontaneous blood-vessel formation, intussusception as formation of new blood vessel by splitting off existing ones, and sprouting angiogenesis. The term "angiogenesis" herein refers also to its modern terminology, i.e. (1) vasculogenesis as formation of vascular structures from circulating or tissue-resident endothelial stem cells, which proliferate into de novo endothelial cells; (2) angiogenesis as formation of thin-walled endothelium-lined structures with/without muscular smooth muscle wall and pericytes; and (3) arteriogenesis as formation of medium-sized blood vessels are also included. Angiogenesis is a normal process in growth, development, and wound healing. It is also a fundamental step in the transition of tumors from a dormant state to a malignant state. The term "angiogenesis" as used herein summarizes all different types and modifications of arterial vessel growth, e.g. increase of capillary density and small vessel formation.

In one embodiment of the present invention, the ischemia is associated with at least one of the group of acute and/or chronic myocardial infarction, chronic heart failure, peripheral vascular occlusive disease, liver and/or kidney ischemia, stroke, bowel ischemia and chronic ulcers of the skin and/or the mucosa.

In one embodiment, the inhibitor is an antagomir or (another) antisense oligonucleotide.

The term "antagomir" as used herein refers to a chemically engineered small RNA that is used to silence miR-24. The antagomir is complementary to the specific miRNA target with either mis-pairing or some sort of base modification. Antagomirs may also include some sort of modification to make them more resistant to degradation. In a preferred embodiment the antagomir is a chemically engineered cholesterol-conjugated single-stranded RNA analogue.

The term "antisense oligonucleotide" as used herein refers to a single strand of DNA or RNA that is complementary to a miR-24 and inactivates miR-24 by binding to it.

In vivo, injections of low concentrations of antagomir (about 5 mg/kg body weight) silence miR-24 expression specifically in the endothelial cell fraction, but not in cardiomyocyte that are only significantly repressed after application of high doses of antagomir (about 80 mg/kg body weight) (see Results). These low doses improve vascularization and heart function after myocardial infarction locally restricted in endothelial cells, i.e. undesired side effects are minimized. Therefore, in a preferred embodiment antagomir is applied in a low dose, preferably less than about 20 mg/kg body weight, more preferably less than about 10 mg/kg body weight, most preferably about 5 mg/kg body weight.

In a mouse model of myocardial infarction, blocking of endothelial miR-24 by systemic administration of a specific antagomir and/or antisense oligonucleotide enhances angiogenesis in the infarct zone and border zone. In addition, blocking of endothelial miR-24 reduces infarct size, preserves cardiac function as measured e.g. by wet lung weight, systolic and diastolic left ventricular dilatation (see Results). Angiogenesis in the infarct zone and border zone comprises in a preferred embodiment an increase of hemoglobin content, invasion of cells as well as small vessel and capillary formation. No significant effects were observed in the remote region of the infarct.

Thus, miR-24 and its antagonists, antagomirs and/or antisense oligonucleotides, serve as spatially restricted therapeutic target and agents, respectively, in the setting of ischemic diseases.

In one embodiment, the antagomir or antisense oligonucleotide is essentially complementary to SEQ ID NO: 1. In a preferred embodiment, the antagomir has a sequence represented by SEQ ID NO: 3 (antagomir-24).

A further aspect of the present invention relates to a direct or indirect microRNA-24 (miR-24) target for use in a method of treatment and/or prevention of ischemia, in a method of prevention of endothelial apoptosis or in a method of induction of angiogenesis.

The term "direct or indirect microRNA-24 (miR-24) target" as used herein refers to a gene whose activity is directly or indirectly influenced (in particular inhibited) by miR-24. A direct miR-24 target (i.e. a gene which is targeted directly by miR-24) is characterized by the presence of miR-24 binding sites (in particular of a miR-24-8 mer seed match) in its 3'-UTR. An indirect miR-24 target commonly functions downstream of one or more direct miR-24 target(s). Preferably, the direct or indirect miR-24 target is regularly expressed in cardiovascular tissues, in particular endothelial cells.

Preferably, the direct or indirect microRNA-24 (miR-24) target is used by activating/increasing its expression and/or activity in cells, in particular endothelial cells.

According to the present invention, the direct or indirect microRNA-24 (miR-24) target is used (preferably, its expression and/or its activity is activated/increased in cells, particularly in endothelial cells) by applying (e.g. transfecting or injecting) its DNA and/or RNA or parts thereof (e.g. comprised in expression constructs or viral and non-viral expression vectors) or by applying the gene product of the respective target or parts thereof, e.g. polypeptides and proteins. Respective methods are known to a person skilled in the art. In a particularly preferred embodiment, the direct or indirect miR-24 targets are overexpressed in endothelial cells by using viral and non-viral, preferably viral expression vectors.

In one embodiment, more than one direct or indirect miR-24 target is used. In another embodiment of the present invention, one or more direct or indirect miR-24 target(s) and a modulator, in particular an inhibitor, of microRNA-24 (miR-24) are used simultaneously.

In one embodiment, the ischemia is associated with at least one of the group of acute and/or chronic myocardial infarction, chronic heart failure, peripheral vascular occlusive disease, liver and/or kidney ischemia, stroke, bowel ischemia and chronic ulcers of the skin and/or the mucosa.

In one embodiment, the direct target is selected from the group of GATA2, PAK4, RASA1, CDKN1B, AMOTL2, H2AFX, RAP1B, AXL, S1PR1, MAGI1, TFPI, ANGPT4 and BMPR2, preferably from the group of GATA2, PAK4, RASA1, AMOTL2, S1PR1, ANGPT4 and BMPR2, even more preferably from the group of GATA2, PAK4 and RASA1.

"GATA2" is also known as GATA binding protein 2. GATA2 is a member of the GATA family of transcription factors that contain zinc fingers in their DNA binding domain. GATA2 is an endothelial-enriched transcription factor that regulates gene expression in hematopoietic cells and is expressed in non-hematopoietic embryonic stem cells and hematopoietic progenitors including early erythroid cells, mast cells, megakaryocytes, and endothelial cells.

"PAK4" is also known as P21(CDKN1A)-activated kinase 4. PAK4 is a member of the family of serine/threonine p21-activating kinases. PAK proteins are effectors that link Rho GTPases to cytoskeleton reorganization and nuclear signaling and serve as targets for the small GTP binding proteins Cdc42 and Rac. PAK4 interacts specifically with the GTP-bound form of Cdc42Hs and weakly activates the JNK family of MAP kinases. PAK4 is also a mediator of filopodia formation and may play a role in the reorganization of the actin cytoskeleton. As can be seen from these examples, PAK4 is implicated in a wide range of biological pathways.

"RASA1" is also known as RAS p21 protein activator 1 or RasGAP (Ras GTPase activating protein). RASA1 is a cytosolic human protein that is part of the GAP1 family of GTPase-activating proteins. RASA1 stimulates the GTPase activity of normal, but not oncogenic RAS p21. RASA1 transfers Ras from its active GTP-bound form to its inactive GDP-bound form by enhancing the endogenous GTPase activity of Ras by a C-terminal GAP domain. RASA1 is also active in mitogenic signal transmission towards downstream interacting partners by N-terminal SH2-SH3-SH2 domains. Mutations leading to changes in the binding sites of either protein are associated with basal cell carcinomas.

"CDKN1B" refers to the cyclin-dependent kinase inhibitor 1B. Cyclin-dependent kinase activation requires association with cyclins (e.g., CCNE1) and phosphorylation by CAK (CCNH), and leads to cell proliferation. Inhibition of cellular proliferation occurs upon association of a CDK inhibitor (e.g., CDKN1B) with a cyclin-CDK complex. Expression of CCNE1-CDK2 at physiologic levels of ATP results in phosphorylation of CDKN1B at thr187, leading to elimination of CDKN1B from the cell and progression of the cell cycle from G1 to S phase. At low ATP levels, the inhibitory functions of CDKN1B are enhanced, thereby arresting cell proliferation.

"AMOTL2" is also known as angiomotin-like 2. Angiomotin (AMOT), the founding member of the motin family, is involved in angiogenesis by regulating endothelial cell motility, and is required for visceral endoderm movement in mice. AMOTL2 is an Fgf-responsive gene. Knockdown of AMOTL2 expression impairs convergence and extension movement, and AMOTL2-deficient cells in mosaic embryos fail to migrate properly. This coincides with loss of membrane protrusions and disorder of F-actin. AMOTL2 partially co-localizes with RhoB- or EEA1-positive endosomes and the non-receptor tyrosine kinase c-Src. AMOTL2 interacts preferentially with and facilitates outward translocation of the phosphorylated c-Src, which may in turn regulate the membrane architecture. AMOTL2 is essential for cell movements in vertebrate embryos.

"H2AFX" is also known as H2AX. It refers to a member of the histone H2A family, 1 of 5 families of histone proteins involved in nucleosomal organization of chromatin.

Hypoxia-induced replication-associated generation of phosphorylated gamma-H2AX in human umbilical vein endothelial cells in vitro and in mice. In mice, this was associated with retinal neovascularization. H2AX-null mice showed decreased endothelial cell proliferation under hypoxic conditions, including deficient hypoxia-induced neovascularization in proliferative retinopathy, in response to hind-limb ischemia, and in tumor angiogenesis. In contrast, developmental angiogenesis is not affected. Endothelial-specific H2AX deletion resulted in reduced hypoxia-driven retinal neovascularization and tumor neovascularization.

"RAP1B" (and RAP1A) belong(s) to a superfamily of RAS-like small GTP-binding proteins involved in cell signaling.

The protein encoded by the gene "AXL" is a member of the receptor tyrosine kinase subfamily. The transforming activity of demonstrates that the receptor can drive cellular proliferation. AXL may involve the stimulation of cell proliferation in response to an appropriate signal, i.e., a ligand that activates the receptor.

"S1PR1" refers to the sphingosine-1-phosphate receptor 1. The lysosphingolipid sphingosine 1-phosphate (S1P) regulates cell proliferation, apoptosis, motility, and neurite retraction. Its actions may be both intracellular as a second messenger and extracellular as a receptor ligand. S1P and the structurally related lysolipid mediator lysophosphatidic acid (LPA) signal cells through a set of G protein-coupled receptors (GPRs) known as EDG receptors (S1PR3).

"MAGI1" belongs to the membrane-associated guanylate kinase (MAGUK) family of scaffolding proteins that assemble multimolecular complexes at subcellular membrane sites. MAGUK proteins share a common modular structure that consists of 1 or 3 PDZ domains, an SRC homology-3 (SH3) domain, and a C-terminal guanylate kinase (GUK) domain. Using the yeast 2-hybrid system to identify proteins that interact with the C terminus of KRasB, MAGI1 was identified. The predicted 1,171-amino acid protein has an N-terminal GUK domain, followed by 2 WW domains and 5 PDZ domains.

"TFPI" refers to tissue factor pathway inhibitor. The gene contains 9 exons and alternative splicing results in the absence of exon 2 in the 5-prime untranslated region of some messages. TFPI-2 may play a role in vessel wall repair by regulating cell proliferation and survival. TFPI is otherwise known as lipoprotein-associated coagulation inhibitor (LACI) because it circulates in association with plasma lipoproteins VLDL, LDL, and HDL. It is a multivalent, Kunitz-type proteinase inhibitor. LACI directly inhibits factor Xa, and, in an Xa-dependent fashion, also inhibits the factor VIIa-tissue factor catalytic complex.

"ANGPT4" refers to angiopoietin-4. Angiopoietins are members of the vascular endothelial growth factor family. The angiopoietins include a naturally occurring agonist, angiopoietin-1 (ANGPT1), as well as a naturally occurring antagonist, angiopoietin-2 (ANGPT2), both of which act by means of the TIE2 receptor. Using homology-based cloning approaches, 2 novel angiopoietins were identified: angiopoietin-3 (ANGPT3) in mouse, and angiopoietin-4 (ANGPT4) in human. Although angiopoietin-3 and angiopoietin-4 are more structurally diverged from each other than are the mouse and human versions of angiopoietin-1 and angiopoietin-2, they appear to represent the mouse and human counterparts of the same gene locus, as revealed in chromosomal localization studies of all the angiopoietins in mouse and human. The structural divergence of angiopoietin-3 and angiopoietin-4 appears to underlie the diverging functions of these counterparts.

"BMPR2" refers to bone morphogenetic protein receptor 2. Bone morphogenetic proteins (BMPs) are a family of proteins that induce bone formation at extracellular sites in vivo. BMPs act on osteoblasts and chondrocytes as well as other cell types, including neuronal cells and endothelial cells, and they play important roles in embryonic development. Members of the BMP family include BMP1 to BMP6, BMP7, also called osteogenic protein-1 (OP1), OP2 (BMP8), and others. BMPs belong to the transforming growth factor beta (TGF-beta) superfamily, which includes, in addition to the TGF-betas, activin/inhibins (e.g., alpha-inhibin), mullerian inhibiting substance, and glial cell line-derived neurotrophic factor. TGF-betas and activins transduce their signals through the formation of heteromeric complexes of 2 different types of serine (threonine) kinase receptors: type I receptors of about 50 to 55 kD and type II receptors of about 70 to 80 kD. Type II receptors bind ligands in the absence of type I receptors, but they require their respective type I receptors for signaling, whereas type I receptors require their respective type II receptors for ligand binding. BMPR2 is a type II receptor for BMPs.

In one embodiment, all above mentioned direct target genes of miR-24, in particular GATA2, PAK4, RASA1, but also AMOTL2, S1PR1, ANGPT4 and BMPR2, exert their anti-apoptotic and angiogenic properties after transfection of the respective cells or cell lines (in particular endothelial cells), e.g. via viral vectors or other commonly known transfection systems.

The inventors have surprisingly found that miR-24 is upregulated in endothelial cells, but not in cardiomyocytes post myocardial infarction and after hypoxic conditions (see Results). In the context of the invention, it was also found that miR-24 overexpression induces apoptosis specifically in endothelial cells, whereas miR-24 antagonism reduces apoptosis in this cell type. In contrast, miR-24 modulation is without effect on apoptosis in other cardiac cell types, such as neonatal cardiomyocytes, the cardiomyocyte cell line H9C2 or cardiac fibroblasts. Hypoxia-induced apoptosis of endothelial cells is attenuated by transfection of miR-24 antagonists, whereas additional transfection of miR-24 precursors exaggerates endothelial apoptosis (see Results).

The inventors have shown by different protein repression assays that miR-24 induces apoptosis specifically in endothelial cells by directly targeting the endothelial-enriched transcription factor GATA2 and the kinases PAK4 and RASA1 (see Results). MiR-24-mediated reduction of PAK4 prevents BAD phosphorylation further contributing to endothelial apoptosis. GATA2 repression leads to a profound increase in apoptosis and impaired endothelial capillary network formation. GATA2 also regulates SIRT1 and HO-1 for which the abbreviation HMOX-1 is also used in the present context.

In summary, miR-24 antagonism attenuates hypoxia-mediated endothelial apoptosis in vitro. Direct miR-24 targets, such as GATA2, PAK4 and RASA1, and/or a modulator, in particular an inhibitor, of miR-24 control a complex network of apoptotic and angiogenic programs and regulate capillary formation in endothelial cells. These important cellular characteristics impact on (neo-) vascularization in vivo, especially after ischemic events (see Results). Thus, miR-24 and its downstream targets in endothelial cells may serve as valuable therapeutic entry points to interfere with endothelial genetic programs leading to improved vascularization and cardiac performance after myocardial infarction. As shown by the data herein, direct miR-24 targets, such as GATA2, PAK4, RASA1, and/or a modulator, in particular an inhibitor, of miR-24 can be used in a method of treatment and/or prevention of ischemia, in a method of prevention of endothelial apoptosis or in a method of induction of angiogenesis.

In one embodiment, the indirect target is selected from the group of phosphorylated BAD, heme oxygenase 1 (HO-1 or HMOX-1), sirt1, bambi, esm1 and ntn4.

The term "BAD" as used herein refers to a distant member of the Bcl-2 family that promotes cell death. In contrast, phosphorylated BAD prevents apoptosis. The term "phosphorylated BAD" as used herein refers to at least one phosphorylation of BAD at any possible phosphorylation site, e.g. Ser112 and/or Ser136.

The term "heme oxygenase 1" or "HO-1", also called "HMOX-1", as used herein refers to an enzyme of the heme catabolism that cleaves heme to form biliverdin. Heme oxygenase activity is induced by its substrate heme and various non-heme substances. Heme oxygenase occurs as two isozymes, an inducible heme oxygenase-1 and a constitutive heme oxygenase-2 that belong both to the heme oxygenase family.

The term "sirt1" as used herein refers to a member of a family of currently seven proteins termed sirtuins. Sirt1 plays a central role in regulating cellular differentiation and senescence and controls metabolic pathways in response to nutrient availability in a wide variety of tissues.

The term "bambi" as used herein refers to a putative transmembrane glycoprotein related to the type I receptors of the transforming growth factor-beta (TGF-beta) family, whose members play important roles in signal transduction in many developmental and pathological processes. However, the encoded protein is a pseudoreceptor, lacking an intracellular serine/threonine kinase domain required for signaling.

The term "esm1" as used herein refers to a secreted protein, which is mainly expressed in the endothelial cells in human lung and kidney tissues. The expression of this gene is regulated by cytokines, and the transcript contains multiple polyadenylation signals and mRNA instability signals. Two transcript variants encoding different isoforms have been found for the coding gene of esm1.

HO-1, bambi, esm1, ntn4, sirt1 and phosphorylated BAD (phospho-BAD) are factors that indirectly regulate and modulate miR-24 effects (i.e. they represent indirect targets of miR-24). As direct targets of miR-24, indirect miR-24 targets can be used in a method of treatment and/or prevention of ischemia, in a method of prevention of endothelial apoptosis or in a method of induction of angiogenesis. In one embodiment, all above mentioned indirect target genes of miR-24 exert their anti-apoptotic and angiogenic properties after transfection of the respective cells or cell lines (in particular endothelial cells), e.g. via viral vectors or other commonly known transfection systems.

Genomic sequences of sirt1 and HO-1 display GATA2 binding sites within their promoter region, and enrichment of the respective DNA sequences after GATA2 immunoprecipitation was detected (see Results). Overexpression of GATA2 strongly induces protein expression of sirt1 and HO-1, whereas siRNA-mediated GATA2 silencing reduces sirt1 and HO-1 expression (see Results). HO-1, which displayed no miR-24 binding site, is regulated by miR-24 via modulation of GATA2 (see Results). HO-1 and sirt1 exert angiogenic, vasoprotective and anti-apoptotic actions in endothelium, and consequently, miR-24-mediated repression of HO-1 and sirt1 via GATA2 resulted in enhanced reactive oxygen species formation in endothelial cells (see Results).

In a search for reversely regulated genes by GATA2 expression modulation, the inventors identified further genes, which are all enriched after GATA-2 ChIP (see Results). These identified genes code bambi, esm1 and ntn4. Like HO-1 and sirt1, the proteins bambi, esm1 and ntn4 show vasoprotective and anti-apoptotic actions in endothelium.

Endothelial miR-24 regulates a network of apoptotic and angiogenic proteins. Thus, miR-24 and its direct and indirect target genes/proteins serve as specific therapeutic targets in the setting of ischemic diseases.

A further aspect of the present invention relates to a precursor of miR-24 (pre-miR-24) for use in a method of treatment of angiogenesis associated with cancer.

The term "precursor of miR-24 (pre-miR-24)" as used herein is meant to refer to synthetic double-stranded, preferably chemically modified, RNA molecules designed to mimic endogenous mature miR-24. Their structure and design are known to a person skilled in the art. They can be introduced into cells using transfection or electroporation parameters similar to those used for siRNAs.

A further aspect of the present invention relates to a siRNA or shRNA against a direct or indirect miR-24 target for use in a method of treatment of angiogenesis associated with cancer, wherein the direct miR-24 target is preferably selected from the group of GATA2, PAK4, RASA1, AMOTL2, S1PR1, ANGPT4 and BMPR2. Preferably, the indirect target is selected from the group of heme oxygenase 1 (HO-1 or HMOX-1), sirt1, bambi, esm1 and ntn4.

Small solid tumors are not vascularized. To spread, they need to be supplied by blood vessels that bring oxygen and nutrients and remove metabolic wastes. Beyond the critical volume of about two cubic millimeters, oxygen and nutrients have difficulties diffusing to the cells in the center of the tumor, causing a state of cellular hypoxia that marks the onset of tumor angiogenesis. Therefore, blood vessel development is an important process in tumor progression and favors the transition from hyperplasia to neoplasia, i.e. the passage from a state of cellular multiplication to a state of uncontrolled proliferation characteristic of tumor cells. Neovascularization also influences the dissemination of cancer cells throughout the entire body eventually leading to metastasis formation.

The inventors have surprisingly found miR-24 to be a molecular factor involved in angiogenesis suitable as a treatment of angiogenesis associated with cancer.

A further aspect of the present invention relates to an in vitro method for diagnosing ischemia or prevalence or disposition for ischemia, comprising the steps of:
a) providing a test sample of a subject comprising endothelial cells;
b) identifying the amount of miR-24 and/or of at least one direct or indirect miR-24 target in the test sample;
c) comparing the amount of miR-24 and/or of the at least one direct or indirect miR-24 target in the test sample with a control sample;
wherein an up-regulation of miR-24 and/or a down-regulation of the at least one direct or indirect miR-24 target in the test sample, in comparison to the control sample, indicates ischemia or prevalence or disposition for ischemia.

In the in vitro method according to the invention providing a test sample of a subject does not comprise the step of taking a sample from a human being, but the steps after taking the sample from a human being and the step of taking samples from non-human beings, preferably non-human mammalians. Providing a test sample or a cell culture includes all necessary or recommended preparation steps, like staining, centrifuging, isolating, purifying, filtrating, fixating, and precipitating.

MiR-24 overexpression inhibits angiogenesis selectively in endothelial cells and controls the apoptotic and angiogenic direct and indirect target genes/proteins, such as GATA2, PAK4 and RASA1 (see Results). Thus, miR-24 and its direct and indirect targets as defined above, in particular GATA2, PAK4 and RASA1, serve as diagnostic markers in the setting of ischemic diseases. The use of more than one of the above markers make the diagnostic method according to the invention more reliable.

A further aspect of the present invention relates to a method for identifying a modulator of miR-24 and/or of a direct or indirect miR-24 target comprising the steps of:
a) providing a cell culture expressing miR-24 and/or a direct or indirect miR-24 target;
b) contacting a candidate substance with the cell culture;
c) assessing the expression and/or activity of miR-24 and/or of the direct or indirect miR-24 target;
d) comparing the expression and/or activity of miR-24 and/or of the direct or indirect miR-24 target of step c) with the expression and/or activity in the absence of the candidate compound,
wherein a difference in the expression and/or activity of miR-24 and/or of the direct or indirect miR-24 target qualifies the candidate substance as a modulator of miR-24 and/or of the direct or indirect miR-24 target.

The "modulator" as used herein regulates and modifies expression and/or activity of miR-24 and of direct or indirect miR-24 targets.

A further aspect of the present invention relates to a pharmaceutical composition or kit comprising a modulator, in particular an inhibitor, of microRNA-24 (miR-24) as defined above, preferably an antagomir and/or an antisense oligonucleotide which is essentially complementary to SEQ ID NO: 1, more preferably an antagomir having a sequence represented by SEQ ID NO: 3.

In one embodiment, the pharmaceutical composition or kit as defined above, further comprises at least one direct or indirect miR-24 target as defined above (e.g. in the form of a polypeptide or polynucleotide/nucleic acid).

A further aspect of the present invention relates to a pharmaceutical composition or kit comprising at least one direct or indirect miR-24 target as defined above (e.g. in the form of a polypeptide or polynucleotide/nucleic acid).

A further aspect of the present invention relates to a pharmaceutical composition or kit comprising a precursor of miR-24 (pre-miR-24) as defined above and/or a siRNA or shRNA against a direct or indirect miR-24 target as defined above.

A further aspect of the present invention relates to an endothelial cell devoid of expressing functional miR-24.

A further aspect of the present invention relates to a non-human, transgenic animal comprising cells devoid of expressing functional miR-24.

Functional miR-24 has its full activity without any reduction or modification.

In a further aspect the present invention relates to a method for treating ischemia in a subject in need thereof, comprising the steps of:
a) identifying a subject suffering from ischemia;
b) inhibiting the expression and/or activity of miR-24 and/or activating/increasing the expression and/or activity of at least one direct or indirect miR-24 target as defined above in cells, in particular endothelial cells, of the subject.

In a still further aspect, the invention relates to a method for preventing ischemia in a subject which is at risk of developing ischemia, comprising the steps of:
a) identifying a subject which is at risk of developing ischemia;
b) inhibiting the expression and/or activity of miR-24 and/or activating/increasing the expression and/or activity of at least one direct or indirect miR-24 target as defined above in cells, in particular endothelial cells, of the subject.

In another aspect the invention relates to a method for preventing endothelial apoptosis in a subject in need thereof, comprising the step of inhibiting the expression and/or activity of miR-24 and/or activating/increasing the expression and/or activity of at least one direct or indirect miR-24 target as defined above in endothelial cells of the subject.

In a further aspect, the present invention relates to a method for inducing angiogenesis in a subject in need thereof, comprising the step of inhibiting the expression and/or activity of miR-24 and/or activating/increasing the expression and/or activity of at least one direct or indirect miR-24 target as defined above in cells, in particular endothelial cells, of the subject.

In preferred embodiments, the expression and/or activity of miR-24 is inhibited by applying an antagomir, preferably antagomir-24 (SEQ ID NO: 3) in a low dose, preferably less than about 20 mg/kg body weight, more preferably less than about 10 mg/kg body weight, most preferably about 5 mg/kg body weight, and the expression and/or activity of at least one direct or indirect miR-24 target as defined above is activated/increased by transfection of a expression construct comprising a nucleic acid, in particular DNA, sequence of the least one direct or indirect miR-24 target or parts thereof.

In a further aspect, the present invention relates to a method for treating angiogenesis associated with cancer in a subject in need thereof, comprising the step of activating/increasing the expression and/or activity of miR-24 (e.g. by applying pre-miR-24) and/or inhibiting the expression and/or activity of at least one direct or indirect miR-24 target as defined above in cancer cells of the subject.

In a preferred embodiment, the step of activating/increasing the expression and/or activity of miR-24 and/or inhibiting the expression and/or activity of at least one direct or indirect miR-24 target as defined above is performed by administering an effective dose of a precursor of miR-24 (pre-miR-24) and/or of an effective dose of a siRNA or shRNA against the at least one direct or indirect miR-24 target as defined above to cancer cells of the subject.

Another aspect of the present invention relates to the use of
  a modulator, in particular an inhibitor, of microRNA-24 (miR-24) as defined above and/or
  a direct or indirect microRNA-24 (miR-24) target as defined above
for the manufacture of a medicament for the treatment and/or prevention of ischemia, of a medicament for the prevention of endothelial apoptosis or of a medicament for the induction of angiogenesis.

A further aspect of the present invention relates to the use of
  a precursor of microRNA-24 (pre-miR-24) and/or
  a siRNA or shRNA against a direct or indirect miR-24 target as defined above
for the manufacture of a medicament for the treatment of angiogenesis associated with cancer.

Figure 5:
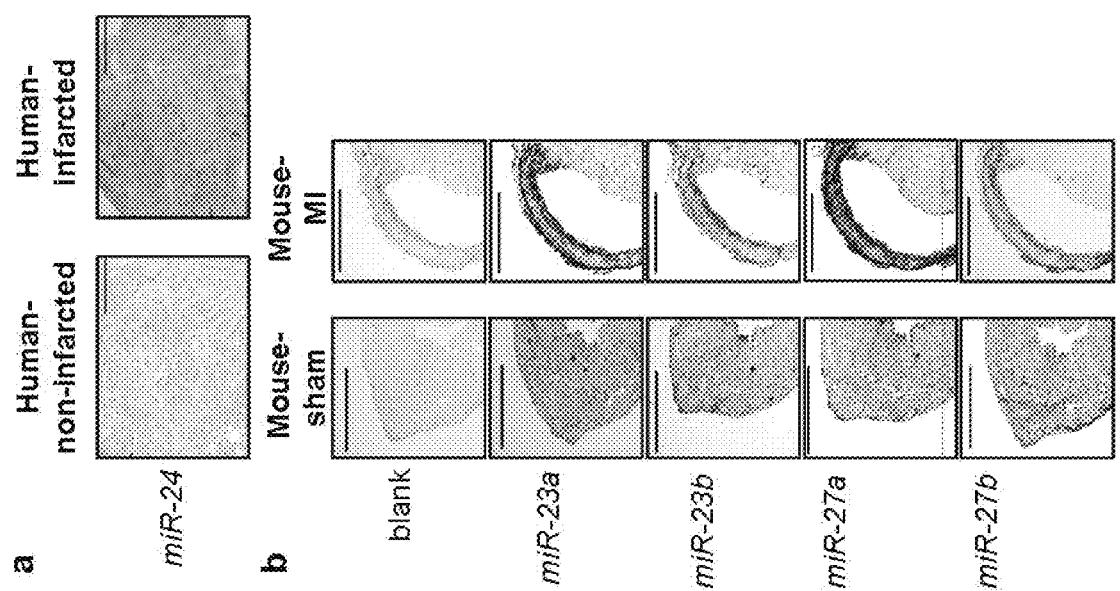
FIG. 5 shows cardiac expression of miR-24 and related miRNAs. (a) In situ hybridization of miR-24 in human non-infarcted and infarcted myocardial biopsies. (b) In situ hybridization of the miR-24 related miRNAs miR-23a, miR-23b, miR-27a and miR-27b in sham-operated and mice 14d after myocardial infarction (MI). Scale bar, 1 mm.

Results 1.1 Selective miR-24 Upregulation in Endothelial Cells after Myocardial Infarction and Hypoxia In vitro, hypoxic conditions (1% $O_2$, 24 h) increased miR-24 expression specifically in endothelial cells (FIG. 1a). A spatiotemporal analysis of miR-24 expression in different fractionated cardiac cell types demonstrated strong induction of miR-24 selectively in endothelial cells isolated from ischemic but not remote myocardium early after myocardial infarction (FIG. 1b,c). Accordingly, only weak miR-24 expression was detected in normal myocardium, whereas the hybridization signal was strongly increased in the periinfarct zone fourteen days post MI in mice (FIG. 1d) and in patients after ischemic cardiac insult (FIG. 5a). Other members of hypoxia-sensitive miRNAs served as controls and were also induced after MI (FIG. 5b).

1.2 Activation of Apoptotic Programs and Impairment of Angiogenic Properties in Endothelial Cells by miR-24

Figure 2:
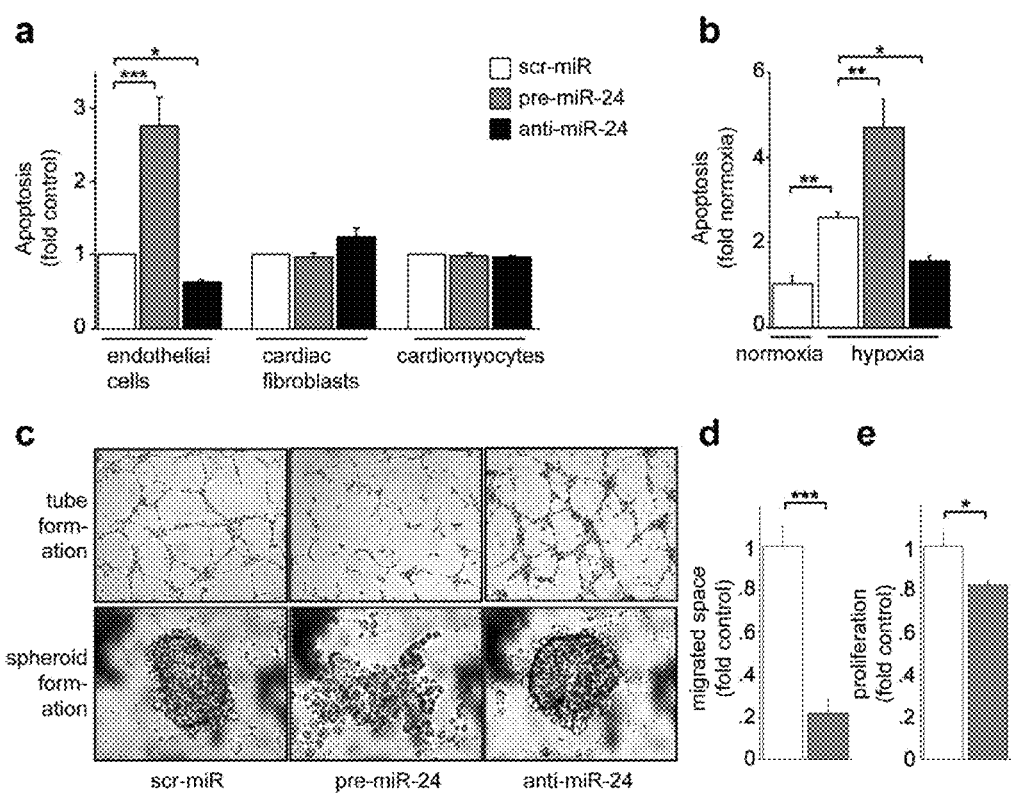
FIG. 2 shows activation of endothelial apoptotic programs and impairment of angiogenic properties by miR-24 (a) Relative changes of apoptotic cells 72 h after transfection of endothelial cells (HUVECs), neonatal rat cardiomyocytes or rat cardiac fibroblasts with scrambled-miR (scr-miR), synthetic miR-24 precursors (pre-miR-24) or miR-24 antagonists (anti-miR-24). (b) Changes of apoptotic endothelial cells after transfection with scr-miR, pre-miR-24 or anti-miR-24 for 72 h and subsequent exposure to hypoxia (1% $O_2$, 24 h) or normoxia (21% $O_2$, 24 h). (c) Tube formation (top) and spheroid formation (bottom) capacity of HUVECs 72 h post transfection with scr-miR, pre-miR-24 or anti-miR-24. (d) Migratory (scratch wound assay) and (e) proliferation (BrdU assay) capacity of HUVECs 72 h after transfection with miR-24 or scrambled controls. n=3-4 experiments per group. Data are mean and s.e.m.; *P, 0.05, P, 0.01, *P, 0.005.
Figure 6:
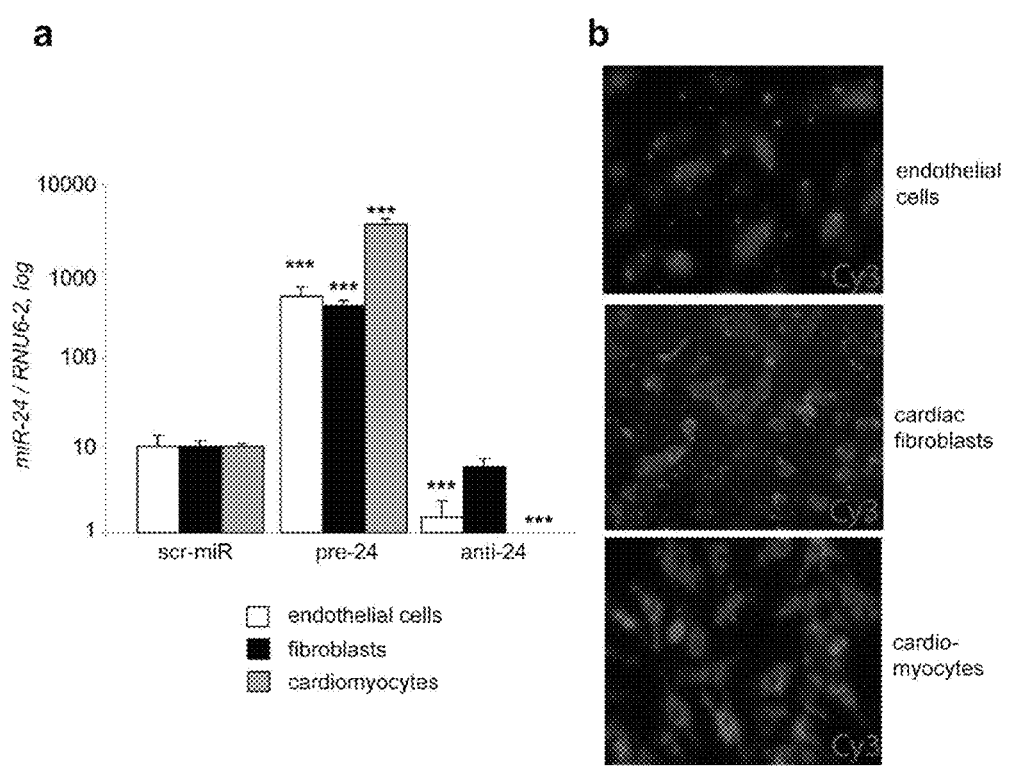
FIG. 6 shows transfection efficacy of miR-24 to cardiovascular cells. Left, expression of miR-24 and RNU6-2 72 h after transfection of scrambled miRNAs (scr-miR, 100 nM), miR-24 precursors (pre-24, 100 nM) or miR-24 antagonists (anti-24, 100 nM) to human umbilical vein endothelial cells, rat neonatal cardiac fibroblasts or cardiomyocytes. Right, Transfection of Cy3-labeled control miRNA precursors (72 h, 100 nM) to different cardiac cell types. n=3 experiments per group. Data are mean and s.e.m.; ***P, 0.005.
Figure 7:
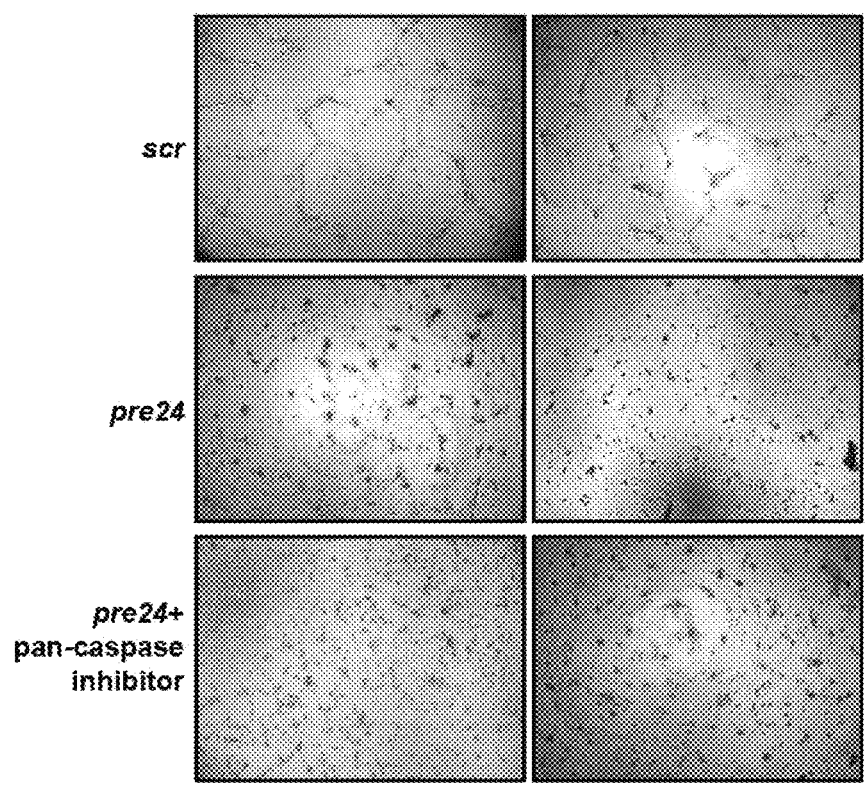
FIG. 7 shows that MiR-24 inhibits endothelial tube formation independently from its pro-apoptotic activity. Endothelial tube formation 72 h after transfection of scrambled miRNAs (scr-miR, 100 nM) or miR-24 precursors (pre-miR-24, 100 nM) in the presence or absence of a pan-caspase inhibitor (Caspase 3 inhibitor I, 100 µm, 72 h). n=4 per group.
Figure 8:
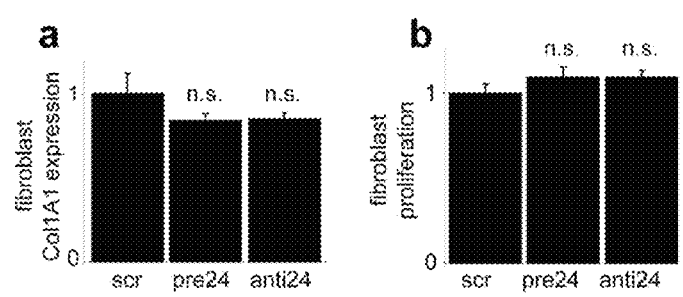
FIG. 8 shows miR-24 effects in cardiac fibroblasts. Collagen type 1 (Col1A1) expression (a) and proliferation capacity (b) in cardiac fibroblasts 72 h after transfection of scrambled miRNAs (scr, 100 nM), miR-24 precursors (pre24, 100 nM) or miR-24 antagonists (anti24, 100 nM). n=3-4 per group. Data are mean and s.e.m.

To characterize miR-24 function, synthetic miR-24 precursors were overexpressed in different cardiac cell types. Transfection efficiency of miRNA precursors and antagonists was monitored by miRNA-specific qRT-PCR and Cy3-labeled pre-miRNAs (FIG. 6a,b). Transfection of miR-24 precursors led to a significant increase of mature miR-24 expression but not of unrelated miRNAs such as miR-33a, miR-412 or miR-510 (FIG. 6a and data not shown). MiR-24 overexpression induced apoptosis selectively in endothelial cells, whereas miR-24 antagonism reduced apoptosis (FIG. 2a). In contrast, miR-24 modulation was without effect on apoptosis in other cardiac cell types, such as neonatal cardiomyocytes, the cardiomyocyte cell line H9C2 or cardiac fibroblasts (FIG. 2a and data not shown), suggesting miR-24 target-enrichment in endothelial cells. Hypoxia-induced apoptosis of endothelial cells was attenuated by blocking endogenous miR-24, whereas overexpression of miR-24 using synthetic precursors exaggerated endothelial apoptosis (FIG. 2b). MiR-24 attenuated tube formation independently from its proapoptotic effects suggesting the potential involvement of multiple target networks (FIG. 2c, FIG. 7). Endothelial spheroid formation, migration in scratch wound assays and proliferation were also impaired by miR-24 (FIG. 2c,d,e). With regard to function in other cardiac cell types, miR-24 overexpression was reported to increase cardiomyocyte hypertrophy in vitro (van Rooil et al., 2006) but its modulation had no effects on fibroblast proliferation or collagen type I expression (FIG. 8).

Figure 9:
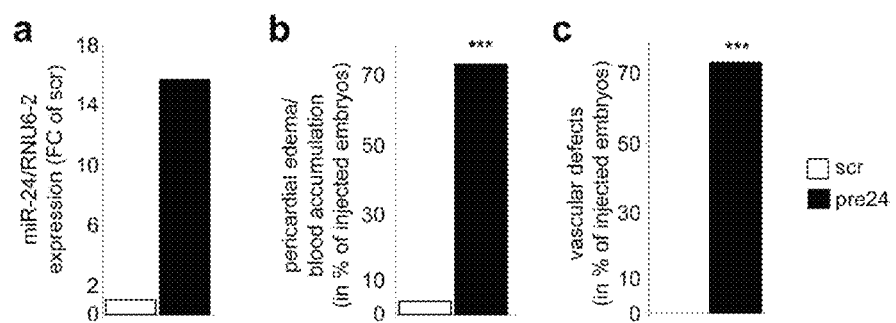
FIG. 9 shows that miR-24 impairs vascularisation in zebrafish embryos. (a) MiR-24 expression in zebrafish embryos 48 h after injection of miR-24 precursors. (b, c) Statistical summary of fish embryos that develop pericardial edema/blood accumulation defects (b) and vascular defects (c). Lateral views of control (scrambled sequence)-(d, e) and pre-miR-24-injected (f-i) tg(flk1:GFP) zebrafish embryos at 48 h post fertilization (hpf). miR-24 overexpressors display impaired and irregular vascularisation patterns (white arrows in (g, i)). Moreover pericardial edema and blood accumulation is seen after miR-24 overexpression (black arrows in (f,h)). ***P, 0.005.
Figure 9:
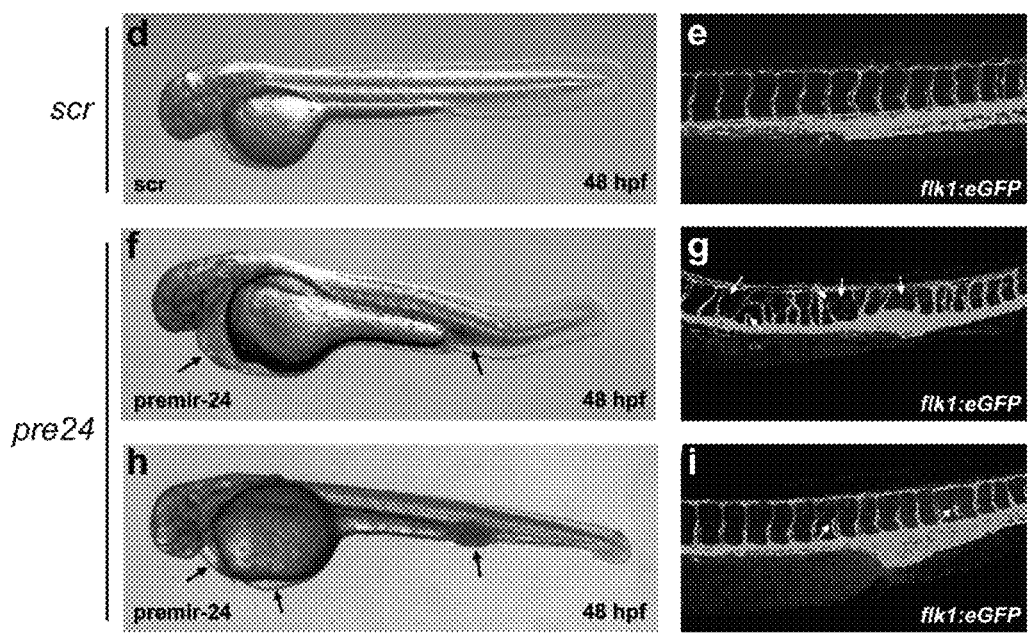

To analyze miR-24 effects in vivo miR-24 precursors were injected into tg(flk:GFP) zebrafish embryos that express green fluorescent protein (GFP) in the vasculature. 48 hpf embryos had increased miR-24 expression levels and presented abnormal vessel architecture and insufficient blood transport, demonstrating miR-24 activation to result mainly in a vascular phenotype, although other cell type specific effects cannot be excluded (FIG. 9)

1.3 MiR-24 Coordinates a Complex Program for Endothelial Apoptosis and Vascularization Capacity by Direct Targets To identify direct miR-24 targets that trigger endothelial apoptosis and impair angiogenic properties, first bioinformatic miRNA target prediction tools were employed. Of all potential miR-24 targets enrichment of endothelial expressed genes was found (see Table 1).

TABLE 1

Predicted microRNA-24 targets

| Gene symbol | Gene name | Evolutionary conserved no. of species (miRBase) | Predicted target (miRBase) | Predicted target (PicTar) | Seed match for miR-24 (TargetScan) |
|---|---|---|---|---|---|
| GATA2 | Endothelial transcription factor GATA2 | 4 | yes | no | 8 mer |
| PAK4 | Serine/threonine-protein kinase PAK 4 | 5 | no | yes | 8 mer |
| RASA1 | Ras GTPase-activating protein 1 | 10 | no | yes | 8 mer |
| CDKN1B | Cyclin-dependent kinase inhibitor 1B (p27Kip1) | 4 | no | yes | 8 mer |
| AMOTL2 | angiomotin like 2 | 3 | no | yes | 8 mer |
| H2AFX | histone family, member X | 5 | yes | yes | 7 mer |
| RAP1B | RAP1B, member of RAS oncogene family | 5 | no | yes | 8 mer |
| AXL | AXL receptor tyrosine kinase | 8 | no | yes | 7 mer |
| S1PR1 | sphingosine-1-phosphate receptor 1 | n.a. | n.a. | n.a. | 8 mer |
| MAGI1 | membrane associated guanylate kinase, WW and PDZ domain containing 1 | 5 | no | n.a. | 8 mer |
| TFPI | tissue factor pathway inhibitor | 5 | no | n.a. | 8 mer |
| ANGPT4 | angiopoietin 4 | 5 | no | n.a. | 8 mer |
| BMPR2 | protein receptor, type II | 6 | no | no | 7 mer |

Figure 3:
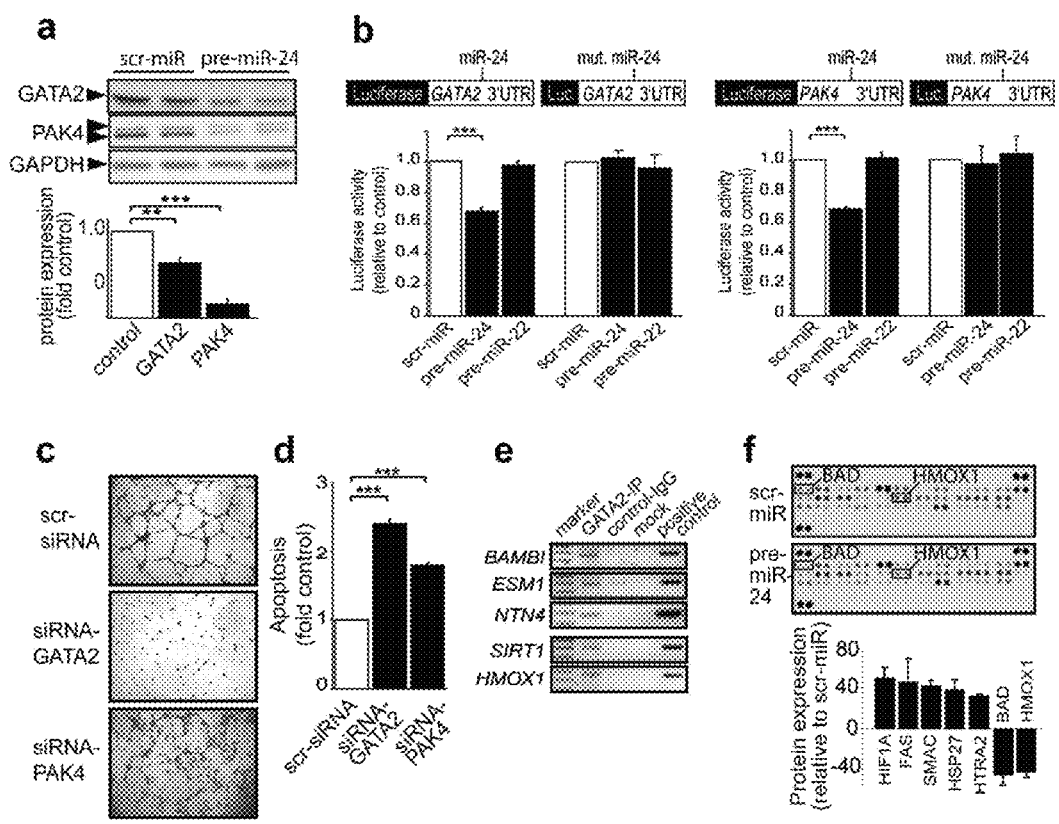
FIG. 3 shows that miR-24 coordinates a complex program of endothelial-enriched targets important for apoptosis and vascularization. (a) Protein expression of GATA2, PAK4, and GAPDH 72 h after transfection with scrambled miRNAs (scr-miR) or synthetic miR-24 precursors (pre-miR-24) to human umbilical vein endothelial cells and statistical summary. (b) Activities of luciferase reporter constructs comprising the normal or mutated 3'UTR regions of GATA2 and PAK4 mRNA relative to beta-Gal control plasmids after transfection of synthetic miRNAs. (c) Tube formation of HUVECs after transfection of scr-siRNA or siRNA against GATA2 or PAK4 24 h after seeding on top of matrigels. (d) Apoptosis of endothelial cells after transfection of scrambled siRNA (scr-siRNA) or siRNAs specific for GATA2 (siRNA-GATA2) or PAK4 (siRNA-PAK4). (e) Chromatin immuno-precipitation of several DNA sequences by GATA2 (GATA2-IP) when compared to appropriate controls. (f) Signal intensity of 35 different apoptosis-related proteins (in duplicates) on Proteome Profiler™ Array membranes (top) and statistical summary (bottom) after hybridization of endothelial protein extracts 72 h post-transfection with scrambled-miRNAs (scr-miR) or synthetic miR-24 precursors (pre-miR-24). (g) Heme oxygenase 1 (HMOX1, left) expression and ratio of phospho-BAD (measured by ELISA) relative to BAD expression (measured by Western blot) (right) in endothelial cells 72 h after transfection with scr-miR, pre-miR-24 or anti-miR-24. (h) pBAD/BAD ratio in endothelial cells 48 h after transfection of scrambled siRNA (scr-siRNA) or siRNA against PAK4 (siRNA-PAK4). (i) Scheme of miR-24-regulated targets and downstream signalling cascades in endothelial cells. Data are mean and s.e.m.; *P, 0.05, P, 0.01, *P, 0.005.
Figure 3:
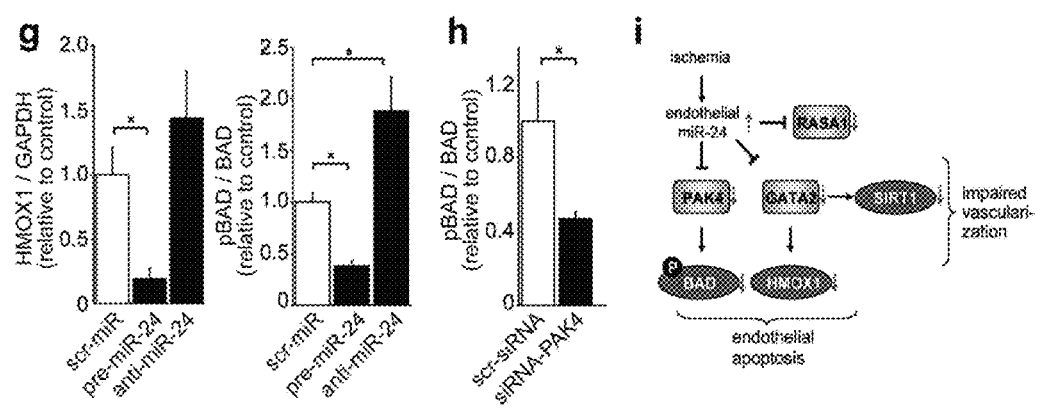
Figure 10:
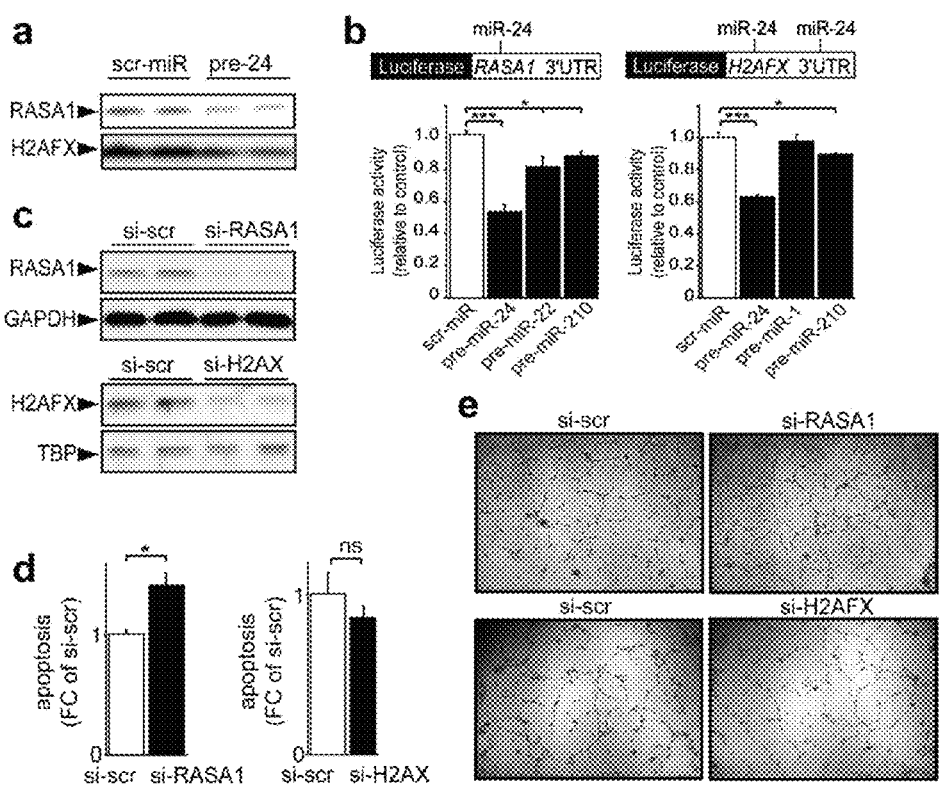
FIG. 10 shows regulation of the further miR-24 targets RASA1 and H2AFX in endothelial cells. (a) Western Blots of RASA1 and H2AFX 72 h after transfection of scrambled (scr-miR) or miR-24 precursors (pre-24). (b) Activities of luciferase reporter constructs comprising the 3'UTR region of RASA1 and H2AFX mRNA relative to beta-Gal control plasmids after transfection of synthetic miRNAs. (c) Western blots of RASA1 and H2AFX 48 h after transfection of specific siRNAs against RASA1, H2AFX or appropriate control siRNAs (si-scr). TBP=TATA box binding protein (nuclear housekeeping protein). (d) Relative changes in apoptosis (Annexin V-assay) and changes in tube formation (e) 48 h after transfection of specific siRNAs against RASA1, H2AFX or appropriate control siRNAs. (f) Effects of a low concentration (10 nM, 72 h) or short time (8 h, 100 nM) of miR-24 overexpression in endothelial cells on target protein expression. n=3-4 experiments per group. Data are mean and s.e.m.; *P, 0.05, ***P, 0.005.
Figure 10:
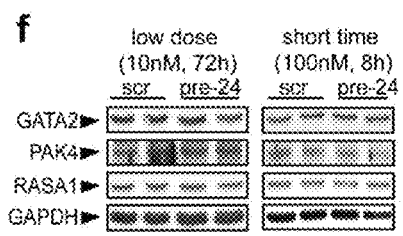
Figure 11:
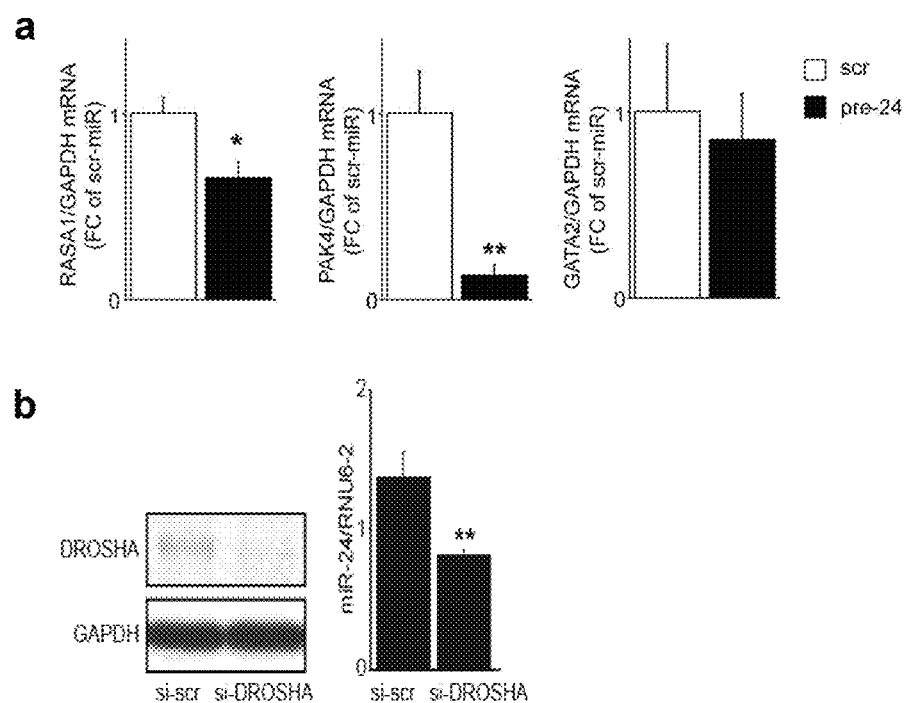
FIG. 11 shows target mRNA expression and Drosha-dependency. (a) mRNA expression levels of miR-24 targets 72 h after transfection of miR-24 precursors (pre-24) or scrambled controls (scr). (b) Expression of miR-24 48 h after silencing of Drosha in endothelial cells. Data are mean and s.e.m.; *P, 0.05, **P, 0.01.

A substantial amount of genes with putative 3'UTR binding sites for miR-24 were detected, which genes cover important functional roles in endothelium including the transcription factor GATA2, the p21-activated kinase PAK4, the RAS p21 protein activator RASA1 and the histone coding gene H2AFX (Table 1). Transfection of primary endothelial cells with miR-24 precursors resulted in protein repression of GATA2, PAK4, RASA1 and H2AFX (FIG. 3a and FIG. 10a). Low concentrations or short transfection times had little effect on target repression (FIG. 10f). PAK4 and RASA1 mRNA levels were also repressed suggesting mRNA degradation (FIG. 11a). MiR-24 expression in endothelial cells was Drosha-dependent (FIG. 11b).

Figure 12:
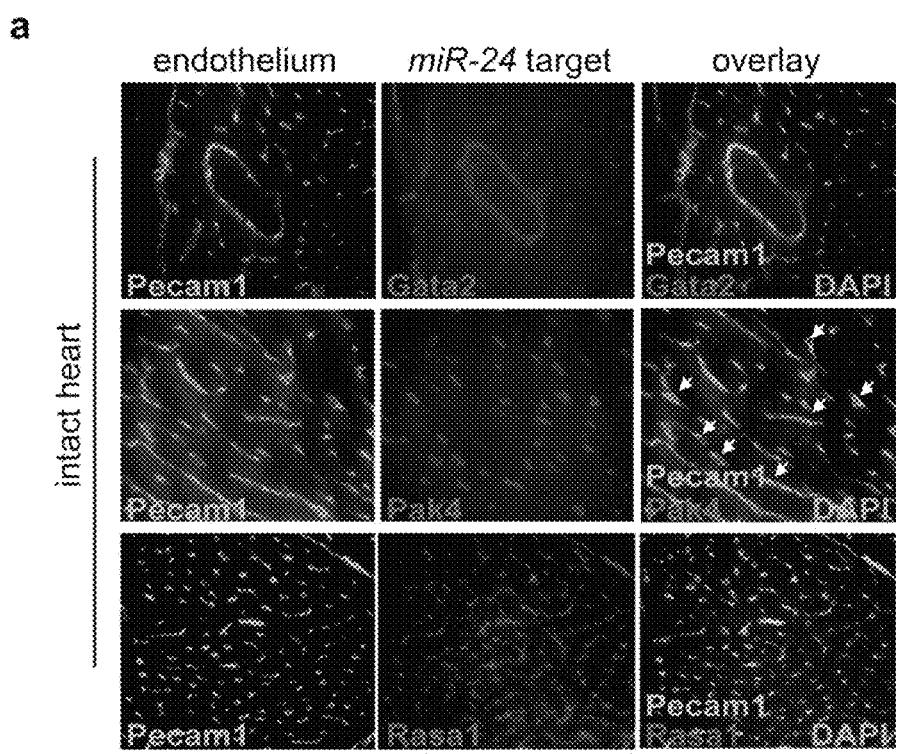
FIG. 12 shows cardiac endothelial expression of miR-24 targets. (a) Localization of endothelial protein Pecam1 and the miR-24 targets Gata2, Pak4 and Rasa1 in sections of mouse hearts. Nuclei were counterstained with 4',6-diamidin-2'-phenylindol-dihydrochlorid (DAPI). White arrows indicate perinuclear region of PAK4 expression in cardiac endothelial cells. (b) Protein expression of miR-24 targets in fractionated cardiomyocytes and cardiac endothelial cells. n=3-4 experiments per group.
Figure 12:
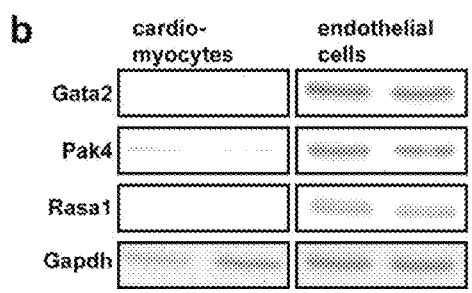

When the respective 3'UTR regions were fused to a luciferase reporter gene and determined luciferase activity in cells transfected with synthetic miR-24 precursors, miR-24 significantly repressed luciferase activity, whereas unrelated miRNAs or miR-24 binding site-mutated 3'UTR target sequences showed no effect (FIG. 3b and FIG. 10b). Thus, GATA2, PAK4, RASA1 and H2AFX were identified as direct targets of miR-24. Immunohistochemical and western blotting analyses revealed enriched cardiac endothelial expression of GATA2, PAK4 and RASA1 (FIG. 12a,b). Silencing of both GATA2 and PAK4 in endothelial cells by siRNA abrogated tube formation capacity and induced apoptosis (FIG. 3c,d). RASA1 silencing induced apoptosis, but did not alter tube formation, whereas no effects were seen after H2AFX downregulation (FIG. 10c-e).

Figure 13:
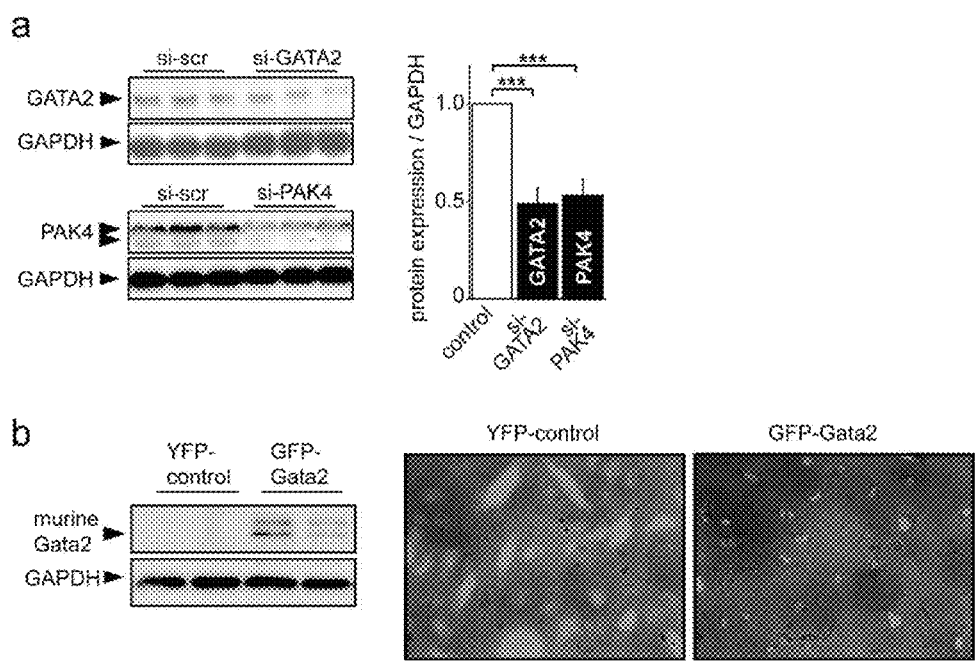
FIG. 13 shows miR-24 target modulation in endothelial cells. (a) Expression of GATA2 and PAK4 48 h after transfection of specific siRNAs against GATA2 or PAK4 or scrambled controls (si-scr). Right, Statistical summary. (b) Gata2 expression three days after transfection of a murine GFP-Gata2 construct or a YFP-labelled control construct to human umbilical vein endothelial cells. Note, cytoplasmic localisation of the control construct and nuclear expression of the GFP-Gata2 construct. n=3-4 experiments per group. Data are mean and s.e.m.; ***P, 0.005.
Figure 14:
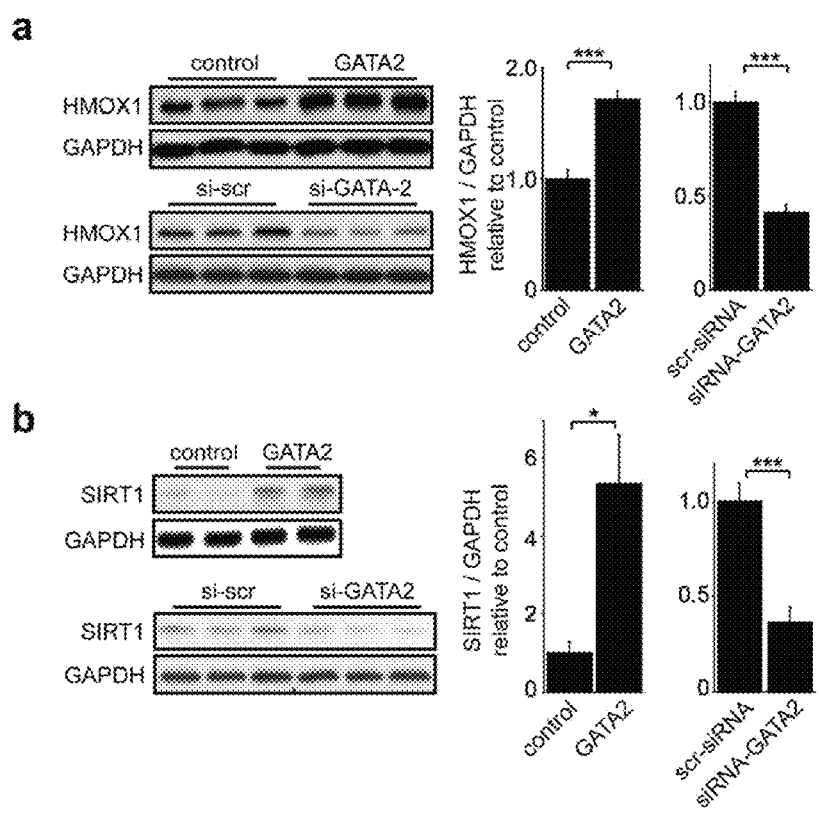
FIG. 14 shows that heme oxygenase-1 (HMOX1) and sirtuin-1 (SIRT1) are regulated by GATA2 in endothelial cells. Western blots of HMOX1 (a) and SIRT1 (b) after up- or downregulation of GATA2 in HUVECs. (c) SIRT1 expression after transfection of increasing doses (m.o.i.) of the adenoviral GATA2 construct to endothelial cells. n=3-4 experiments per group. Data are mean and s.e.m.; *P, 0.05; ***P, 0.005.
Figure 14:
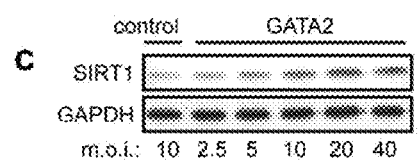
Figure 15:
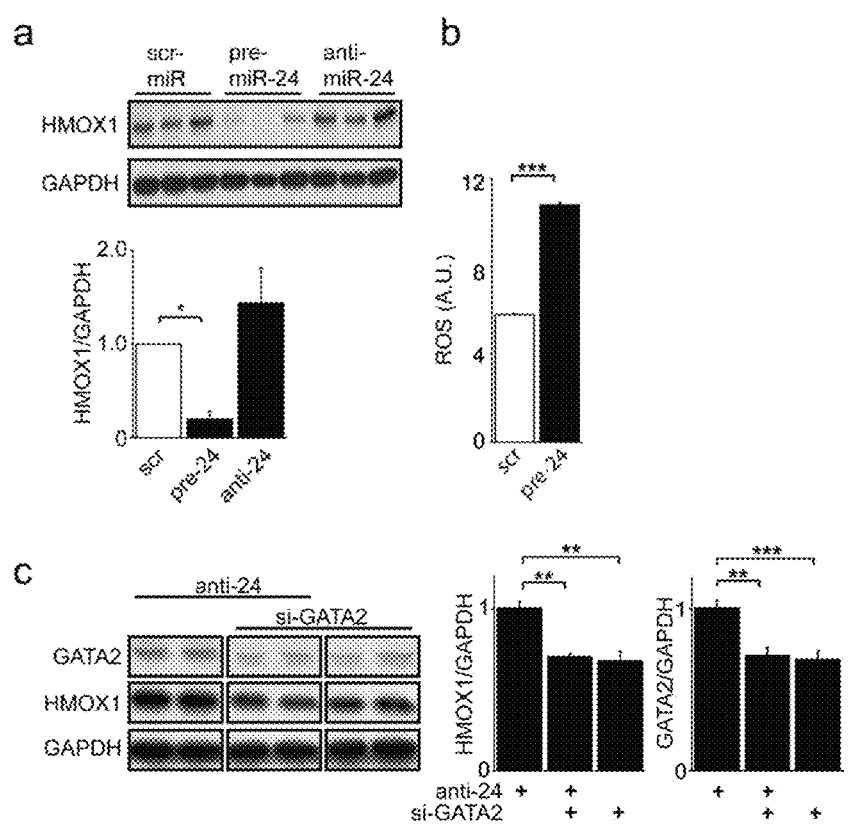
FIG. 15 shows that miR-24 regulates HMOX1 expression via GATA2 and increases reactive oxygen species (ROS) formation in endothelial cells. (a) HMOX1 expression is regulated by miR-24 in endothelial cells. (b) FACS-based analysis of ROS formation 72 h after transfection of synthetic miR-24 precursors (pre-24) or scrambled controls (scr) to HUVECs. (c) GATA2 and HMOX1 expression in endothelial cells after miR-24 inhibition and/or GATA2 silencing. n=3-4 experiments per group. Data are mean and s.e.m.; *P, 0.05, P, 0.01, *P, 0.005.

To understand the cellular changes upon miR-24 target regulation, the downstream signalling cascades of the direct miR-24 target GATA2 was further investigated. Global transcriptome analysis after viral overexpression or silencing of GATA2 in endothelial cells (FIG. 13a,b) was combined with chromatin-immunoprecipitation (ChIP) to enrich genomic sequences bound by GATA2 (FIG. 3e). For GATA2 overexpression a murine GFP-GATA2 construct was used (FIG. 13b). Reciprocally regulated genes after GATA2 modulation were searched for and further genes important in angiogenesis, e.g. BAMBI, ESM1 and NTN4, were identified which display GATA2 binding sites in their respective promoters and were enriched after GATA2-ChIP (FIG. 3e). To identify the proteins mediating pro-apoptotic action of endothelial miR-24, endothelial protein extracts after transfection of scrambled miRs or synthetic miR-24 precursors were hybridized to a protein-microarray spotted with antibodies for proteins involved in apoptosis. A number of pro-apoptotic proteins were upregulated, e.g. HIF1A (hypoxia-inducible factor-1 alpha) and FAS, whereas strong reduction of BAD (Bcl-XL/Bcl-2-associated death promoter) and HMOX1 (heme-oxygenase-1) (FIG. 3f,g left) was found. Genomic sequences of HMOX1 and SIRT1 displayed GATA2 binding sites within their promoter region (data not shown) and enrichment of the respective DNA sequences was detected after GATA2 immunoprecipitation (FIG. 3e). In line with these observations, GATA2 overexpression strongly induced protein expression of HMOX1 and SIRT1, whereas siRNA-mediated GATA2 silencing reduced expression (FIG. 14a-c). HMOX1, which displayed no miR-24 binding site, was regulated by miR-24 via modulation of GATA2 (FIG. 15a,c). MiR-24-mediated repression of HMOX1 was found to result in enhanced reactive oxygen species formation in endothelial cells (FIG. 15b).

Figure 16:
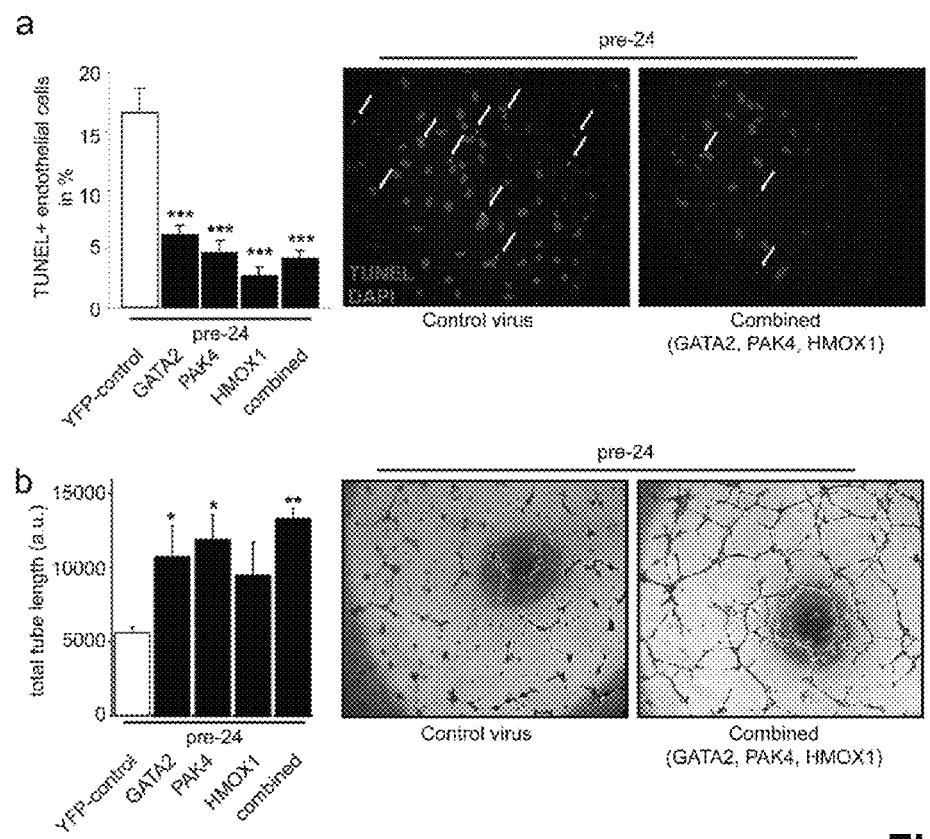
FIG. 16 shows rescue of miR-24-mediated apoptosis and impaired angiogenesis by miR-24 target overexpression. (a) Terminal deoxynucleotidyl transferase (TdT) to transfer biotin-dUTP (TUNEL)-positive cells (white arrows) and (b) total endothelial tube length 48 h after transfection of miR-24 precursors (pre-24, 20 nM) to pre-transfected (−24 h) (YFP-control construct, GATA2-, PAK4 and/or HMOX-1 construct; each miR-24-resistant) human endothelial cells. n=3-6 experiments per group. Data are mean and s.e.m.; *P, 0.05, P, 0.01, *P, 0.005.

MiR-24 overexpression led to a reduction of phosphorylated BAD (pBAD), whereas miR-24 antagonism induced the pBAD/BAD ratio (FIG. 3g). Repression of the direct miR-24 target PAK4 resulted in reduced BAD phosphorylation (FIG. 3h and FIG. 13a) contributing to increased apoptosis in endothelial cells (FIG. 3d). Overexpression of miR-24 resistant GATA2, PAK4 and HMOX1 rescued miR-24-mediated endothelial apoptosis and impaired tube formation capacity (FIG. 16a,b).

In summary, a network of direct and indirect miR-24 targets was identified regulating apoptosis and angiogenic properties in endothelial cells, important cellular characteristics that impact on (neo)vascularization in vivo, especially after ischemic events (FIG. 3i).

Figure 4:
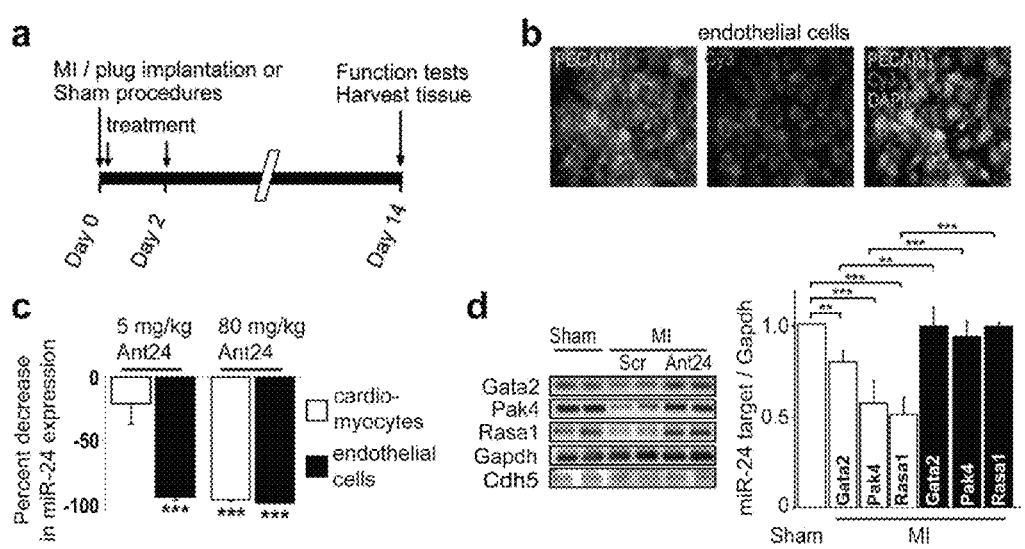
FIG. 4 shows that antagomir-24 treatment improves vascularization and preserves cardiac function after myocardial infarction. (a) Design of the antagomir in vivo study. (b) Uptake of Cy3-labeled antagomirs in endothelial cells (HUVECs, 10 µg/ml, 24 h). (c) Percent decrease of miR-24/Rnu6-2 in fractionated cardiomyocytes and CD146+ endothelial cells after treatment with 5 mg/kg or 80 mg/kg (each at day 0 and 2) of antagomir-24. Note, endothelial miR-24 was significantly reduced after dosing with 5 mg/kg, whereas in cardiomyocytes miR-24 was only significantly repressed after application of high doses. (d) Expression of the miR-24 targets Gata2, Pak4 and Rasa1 in fractionated CD146+ cardiac endothelial cells obtained from Sham-operated mice and mice after MI post treatment with scrambled antagomir (Scr) or antagomir-24 (Ant24). Gapdh and endothelial-specific VE-cadherin (Cdh5) served as controls; Right, statistical summary. (e) Left, capillary (Pecam1) and arteriolar (Acta2) density in cardiac sections of the periinfarct region fourteen days after myocardial infarction and after treatment with antagomirs against a scrambled sequence (Scr) or miR-24 (Ant24). Right, statistical summary of the number of Pecam1+ capillaries and Acta2+ arterioles in the periinfarct and remote area. (f) Cardiac function as fractional shortening (FS) measured by echocardiography fourteen days after Sham-operation or myocardial infarction (MI). (g) Diastolic and (h) systolic left ventricular diameter (LVd and LVs). (i) Lung wet weight after Sham-operation or MI. n=3-9 experiments/animals per group. For e, f, g, h, i at least n=6 animals per group. Data are mean and s.e.m.; *P, 0.05, P, 0.01, *P, 0.005.
Figure 4:
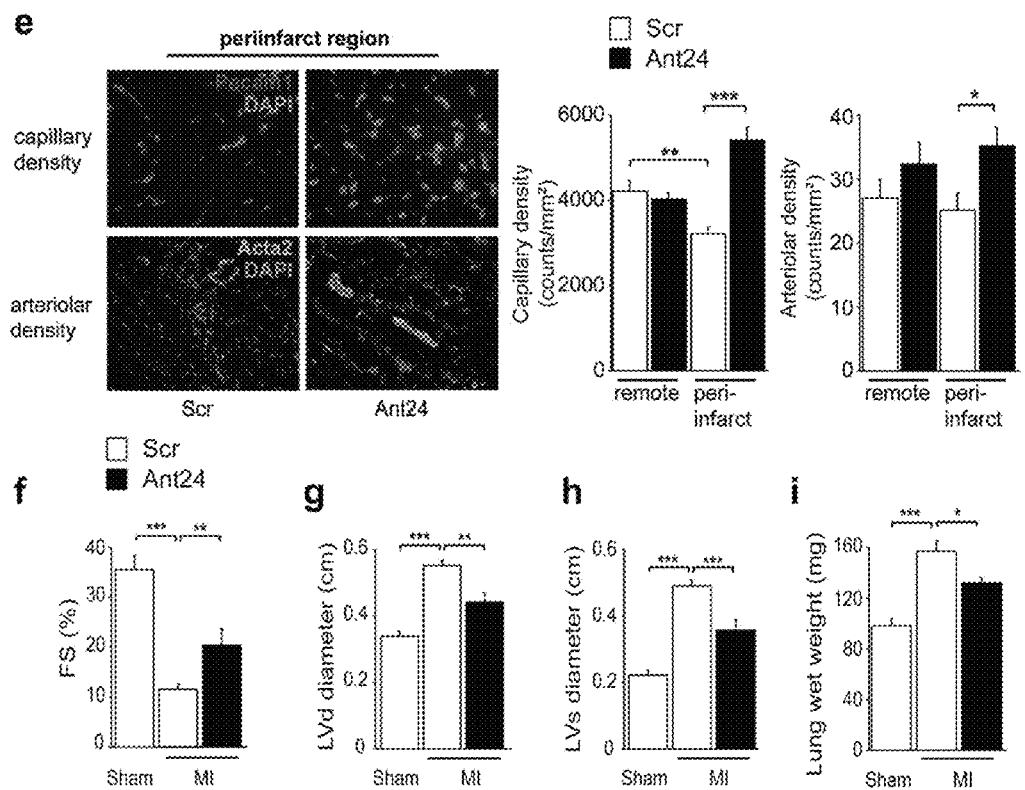
Figure 17:
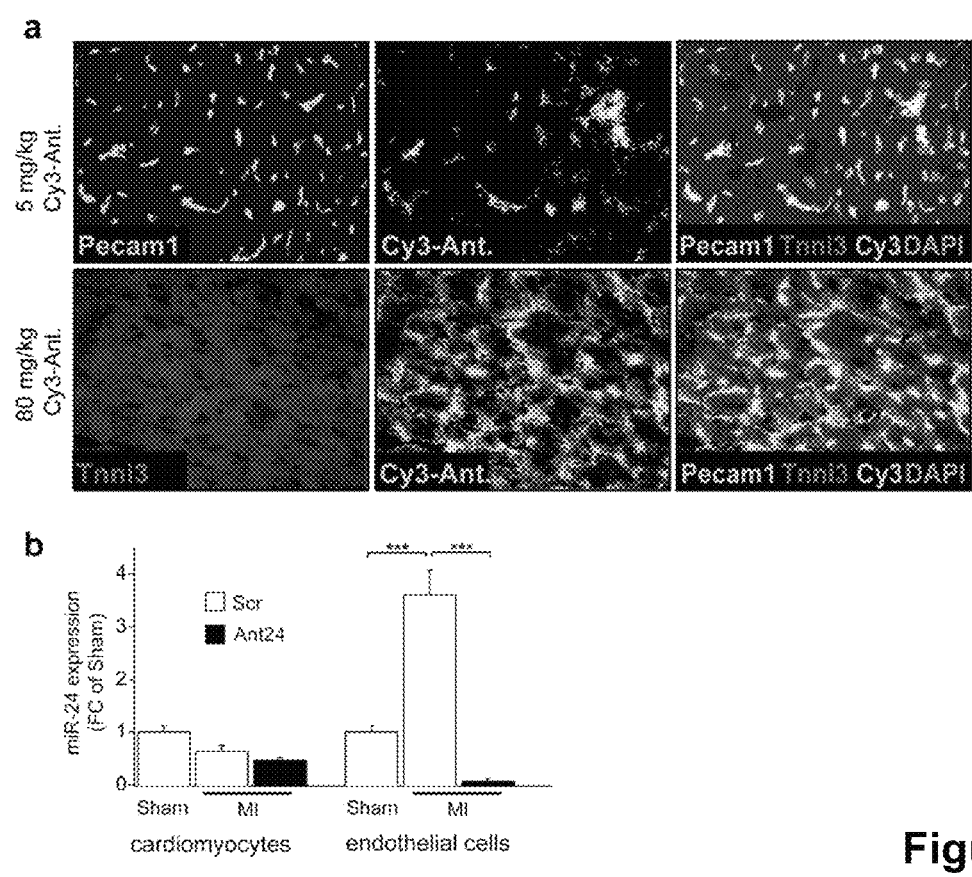
FIG. 17 shows cell-specific cardiac uptake of antagomirs. (a) Primary deposition of Cy3-labeled antagomirs to Pecam1-positive endothelial capillaries after injection of a low dose (5 mg/kg) or homogenous cardiac uptake after treatment with 80 mg/kg (high dose). (b) MiR-24 expression in fractionated cardiomyocytes and cardiac endothelial cells 14 d after myocardial infarction (MI). Animals were treated at d0 and d2 with either 5 mg/kg scrambled antagomir (Scr) or antagomir against miR-24 (Ant24). n=3 experiments per group. Data are mean and s.e.m.; ***P, 0.005.

1.4 Specific Targeting of Cardiac Endothelial Cells by Low Antagomir Concentrations To study the effects of miR-24 on vascularization in vivo, chemically engineered cholesterol-conjugated single-strand RNA analogues (antagomirs) targeting miR-24 or scrambled controls were injected into mice (FIG. 4a). In initial experiments, Cy3-labeled antagomirs were found to be effectively taken up by endothelial cells in vitro (FIG. 4b). Because it was desired to target mainly the endothelial cell fraction in vivo, first titration experiments with Cy3-labeled antagomirs were performed to achieve preferential delivery to endothelial cells. Injection of a Cy3-labeled antagomir at a low dose (5 mg/kg) mainly resulted in cellular uptake in cardiac endothelial cells, whereas injection of a high dose (80 mg/kg) led to a strong homogeneous uptake of all cardiac cells, including cardiomyocytes (FIG. 17a). Consequently, injections of low doses of an antagomir (5 mg/kg, day 0 and 2) against miR-24 were found to repress miR-24 but not unrelated miRNAs mainly in fractionated endothelial cells obtained from healthy and ischemic heart tissue (FIG. 4a,c, FIG. 17b and data not shown).

Figure 18:
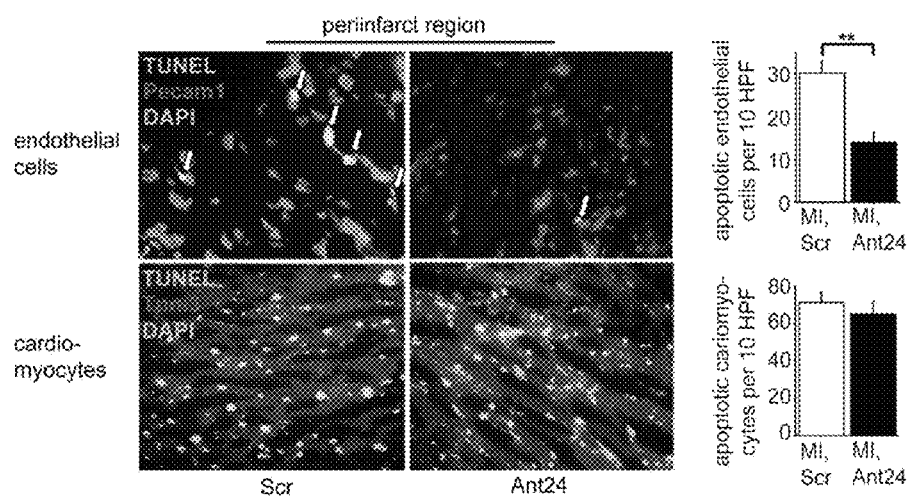
FIG. 18 shows prevention of endothelial apoptosis in vivo and reduction of infarct size by antagomir-24 treatment. Apoptotic endothelial cells (TUNEL$^+$/Pecam1$^+$ cells; top) and apoptotic cardiomyocytes (TUNEL$^+$/Tnni3$^+$ cells; bottom) within the periinfarct region 14 d after myocardial infarction (MI) and treatment with scrambled antagomirs (Scr) or antagomir-24 (Ant24). Right, Statistical summary. n=6-8 experiments per group. Data are mean and s.e.m.; **P, 0.01.
Figure 19:
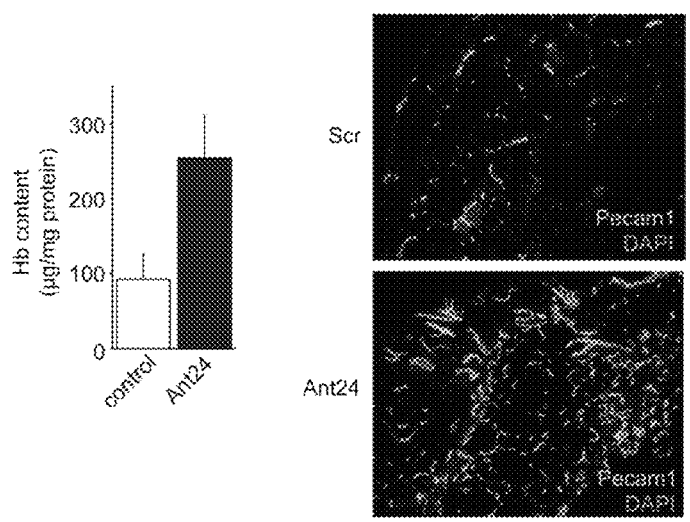
FIG. 19 shows that antagomir-24 treatment increases vascularization of implanted matrigel plugs. Haemoglobin (Hb) content (left) and vascularization of matrigel plugs (right) 14 days after implantation and treatment with 2 doses (day 0 and 2) of antagomir-24 (Ant24) or scrambled antagomir (Scr). n=3-4 experiments/animals per group.
Figure 20:
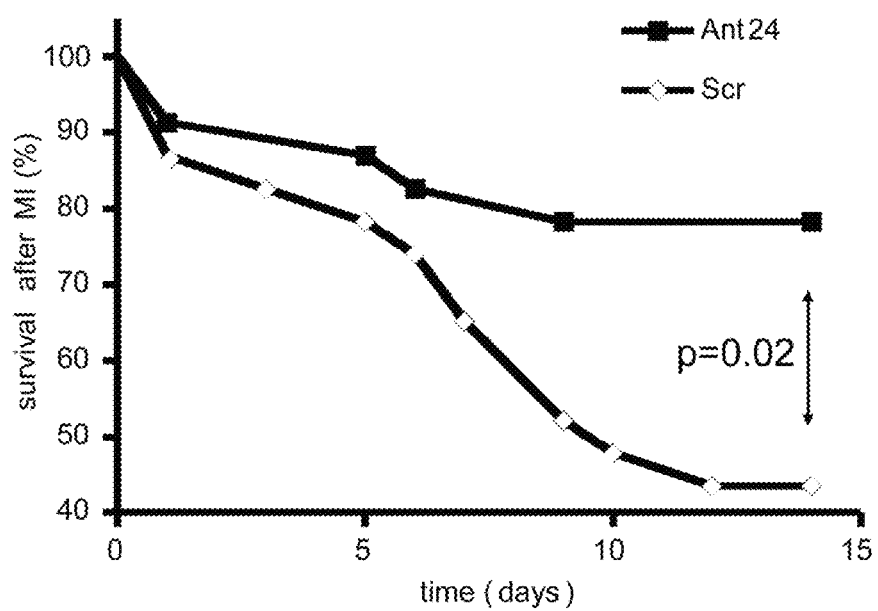
FIG. 20 shows that miR-24 antagonism improves survival after myocardial infarction. Kaplan-Meier survival analysis of mice after myocardial infarction (MI) and treatment (d0 and d2 with each 5 mg/kg antagomir) with scrambled (Scr) or antagomir-24 (Ant24). n=23 per group. P=0.02 between both groups.

1.5 Antagomir-24 Treatment Improves Vascularization and Preserves Cardiac Function after Myocardial Infarction Subsequently, the effects of endothelial miR-24 antagonism in a mouse model of myocardial infarction were tested. The miR-24 targets GATA2, PAK4 and RASA1 were downregulated in fractionated cardiac endothelial cells post-MI, whereas antagomir-24 treatment completely normalized expression (FIG. 4d). Immunohistochemical studies revealed lower capillary density and a higher amount of apoptotic cardiomyocytes and endothelial cells in the periinfarct zone when compared to remote myocardium (FIG. 4e and FIG. 18). In contrast, endothelial apoptosis measured by TUNEL$^+$/Pecam1$^+$ cells was reduced and capillary as well as arteriolar density was increased in the periinfarct region after miR-24 antagonism, whereas no changes were observed in the remote myocardium (FIG. 4e, FIG. 18). Improved capillary density correlated with significant smaller infarct size 14 d after MI (control 0.54±0.06 vs. antagomir-24: 0.38±0.03, p<0.05). Increased invasion of cells and capillary network formation was also detected, as well as higher haemoglobin contents in implanted matrigel plugs in mice fourteen days after treatment with an antagomir against miR-24 demonstrating improvement of angiogenesis (FIG. 19). MI led to an impairment of cardiac function fourteen days after intervention (FIG. 4f). Systolic and diastolic left ventricular diameter as well as lung wet weight increased after MI (FIG. 4g-i). In contrast, immediate treatment after MI with an antagomir against miR-24 (day 0 and 2) improved cardiac function and attenuated pulmonary congestion and left ventricular dilatation (FIG. 4a,f,g,h,i). Survival of MI-animals was significantly improved by miR-24 antagomir treatment (FIG. 20; survived animals at d14: scrambled antagomir, 43.5% vs. antagomir-24, 78.3%, P=0.02). To exclude significant off-target effects and to confirm specificity of antagomir-24, an antagomir against a scrambled sequence was injected, which did not affect miR-24 expression, infarct healing or plug vascularization (FIG. 4c,e,f,g,h,i and FIGS. 17b,18,19).

1.6 Summary miR-24 was identified as a critical regulator of endothelial cell survival and angiogenesis. Direct and indirect miR-24 targets including GATA2 (regulating SIRT1 and HMOX1), PAK4 (regulating BAD phosphorylation) and RASA1 were found, that together control a complex network of apoptotic and angiogenic programs in endothelial cells. Application of antagomirs permitted silencing of miR-24 expression predominantly in endothelial cells in vivo, resulting in reduced endothelial apoptosis, enhanced vascularization, decreased infarct size and improved cardiac function after MI. Thus, miR-24 and its downstream targets can serve as valuable therapeutic entry points to interfere with endothelial genetic programs and thereby improve vascularity and cardiac performance after ischemic injury.

Methods 2.1 Cultivation of Cardiovascular Cells

Human umbilical vein endothelial cells (HUVECs) were cultured in EGM2 media supplemented with 20% (v/v) fetal calf serum (FCS) and supplements (all reagents from Cambrex Lonza, UK). Cells were grown in a humidified atmosphere at 5% $CO_2$ and 37° C. Neonatal rat cardiomyocytes and cardiac fibroblasts were isolated and cultured as described previously (Thum, 2008; Thum et al., 2007).

2.2 Fractionation of Cardiac Cell Types from Heart Tissue

The thorax of mice was opened and the aorta was cannulated. After washing with 37° C. PBS, the heart together with the cannula was removed and perfused with a collagenase solution for 5 min (Joklik MEM medium supplemented with 10 mM butanedione monoxime, 20 µM calcium chloride, 1 mg/ml collagenase II). Then the heart was placed in 37° C. pre-warmed collagenase solution for further 25 min and was subsequently minced and filtered through a nylon mesh (200 µm pore size). Then, cardiomyocytes and cardiac fibroblasts were separated by a sedimentation step as described (Thum, 2008). Within the non-cardiomyocyte cell fraction retained in the supernatant an incubation step with CD146-antibodies coupled to microbeads was performed and subjected to magnetic affinity cell sorting according to the manufacturers' recommendations (Mouse CD146 microbead endothelial isolation kit, Miltenyi Biotec, Germany). Purity of fractionated cells was assessed by cell specific stainings (Thum, 2008) and RT-PCR analysis of endothelial-specific miR-126 and cardiomyocyte-specific miR-499 (see below).

2.3 mRNA/RNA Isolation, miRNA-RT-PCR and Global Transcriptome Analysis

RNA isolation was done with TRIzol reagent (Invitrogen, Germany) or the mirVana miRNA Isolation Kit (Ambion, USA) according to manufacturers' instructions. For detection of miRNAs in samples different TaqMan MicroRNA assays (Applied Biosystems, USA) were applied (see Table M1). The small RNA molecule U6 small nuclear (Rnu6b) was amplified as a control. RT-PCR analysis was performed in an ICycler (Bio-Rad, Germany). The organ panel for miR-24 expression analysis was purchased from BioCat (Heidelberg, Germany). To assess RNA integrity for downstream array analysis total RNA was subjected to capillary chromatography in an Agilent bioanalyzer 2100 (Agilent, USA). Gene array analysis was performed using the Affymetrix Genechip system according to the manufacturer's instructions and using Human Gene 1.0ST arrays (Affymetrix Systems, USA). Further microarray analyses and data handling were performed using the XRAY software package (Biotiquesystems, USA).

2.4 RT-PCR mRNA Analysis

For detection of rat collagen I (Col-1A1) mRNA expression RT-PCR was performed (oligonucleotide sequences in Table M2). RNA isolation was done with TRIzol reagent (Invitrogen, Germany) and reverse transcribed with iScript Select cDNA Synthesis Kit (Bio-Rad, Germany). RT-PCR analysis was performed in an ICycler (Bio-Rad, Germany) with the following conditions: 94° C. 2 min, then [94° C. 15 sec, 60° C. 30 sec, 72° C. 40 sec]×40, followed by melt curve analysis. Data were normalized to house-keeping gene GAPDH by the use of standard curves.

2.5 In Situ Hybridization

In situ hybridization directed against miR-24 was carried out using a cocktail of four digoxigenin (DIG)-labelled LNA-residue-containing oligodeoxynucleotide probes where the LNA modifications were placed at different positions within the miR-24-complementary sequence (Table M3). Heart tissues were collected, immersed in 4% formaldehyde solution for 24 h, then placed in 0.5 M sucrose for 48 h. Tissues were frozen in a dry-ice/ethanol bath, mounted for sectioning using a cryostat (Leica). Sections of 10 µm were mounted on Super-Frost Plus glass slides (Thermo Fisher Scientific). The tissue sections were further fixed with formaldehyde-EDC. For probe hybridization, 32 pmol of LNA probe cocktail (8 pmol of each probe) were applied in 100 µl of hybridization solution per slide. Probes were hybridized overnight at 51° C., and processing was continued using a series of enzymatic reactions with the product being a colorimetric precipitate of 5-bromo-4-chloro-3-indolyl phosphate (BCIP) and nitro blue tetrazolium (NBT). Images were captured on an Olympus BX50 microscope equipped with a DP70 camera and Olympus DP controller software. Next to miR-24, also in situ hybridization for miR-23a, miR-23b, miR-27a and miR-27b were performed (Table M3).

2.6 Transfection Assays

Transient liposomal transfection of small-inhibitory RNAs (siRNAs) or microRNAs was done according to manufacturers' instructions. Briefly, cells were splitted one day before transfection to reach 60-70% confluence on day of transfection. Specific siRNAs/miRNAs and control siRNA/miRNA and Lipofectamine 2000 (Invitrogen, Germany) were mixed separately and incubated for 5 min with Opti-MEM I (Invitrogen) media. Complexes were added together and incubated for 20 min. Media was changed to antibiotic-free media before adding liposomal siRNA complexes (final concentration 150 nM for siRNA and 100 nM for miRNAs). Cells were incubated for 4 h before changing the media to fresh medium. Silencing of proteins or miRNA targets was monitored 48 h (siRNA) or 72 h (miRNAs) post transfection by western blot analysis. Specific details about the used siRNAs and miRNAs are given in Table M4.

2.7 Apoptosis Detection

Apoptosis was measured with the Annexin-V-Fluos kit from Roche Diagnostics (Penzberg, Germany) according to manufacturers' instructions. FACS analysis was performed on a FACSCalibur (BD Biosciences, USA).

2.8 Western Blotting

Western blot analysis was performed with 10-40 µg total protein. Protein was blotted onto PVDF membrane in Mini Trans-Blot electrophoretic transfer cell (Bio-Rad, Germany). Afterwards different antigens were detected by appropriate antibodies (see Table M5).

2.9 Apoptosis Protein Array

Apoptosis array data were generated by applying a human apoptosis array kit (ARY009, R&D, USA). 200 µg protein from a pool of three samples were incubated with antibody-coated membranes following manufacturers' instructions. Various regulated proteins were then validated by Western blotting.

2.10 ELISA

For phospho-Bad (Ser112) detection in cell culture samples we applied a PathScan Phospho-Bad (Ser112) Sandwich ELISA Kit (#7182, Cell Signaling, USA) according to manufacturers' instructions. Phospho-Bad levels were related to total BAD expression levels as obtained by Western Blotting.

2.11 Detection of Reactive Oxygen Species (ROS)

The redox-sensitive, cell-permeable fluorophore dihydroethidium (DHE) becomes oxidized in the presence of $O_2^-$ to yield fluorescent ethidium. Thus, dye oxidation is an indirect measure of the presence of reactive oxygen intermediates. MiRNA-transfected HUVECs were incubated with DHE (2.5 µM) for 30 min. After washing, HUVECs were immediately analyzed with FACS (FACS Calibur, BD Bioscience).

2.12 Tube Formation Assay

Transfection or transduction of cultured cells was done as mentioned before. Then, cells were harvested and 15.000 cells were seeded on top of Matrigel coated chamber slides (BD, Germany). After 6-8 h and 24 h pictures were taken on a Zeiss Axiovison microscope (Jena, Germany). In selected experiments the pan-caspase inhibitor Caspase 3 inhibitor I (Calbiochem, Germany, 100 µM, 72 h) was employed.

2.13 Spheroid Formation Assay miRNA-transfected HUVECs were trypsinized, collected in EBM-2 medium containing 20% FCS and 20% Methocel (Sigma, Germany). For spheroid formation, 750 cells in 150 µl medium were plated per one well in 96-well round bottom plate for non-adherent cells and cultivated overnight at 37° C., 5% CO2. Next day, the spheroid formation was visualized using Zeiss Axiovert 135 microscope at 10× magnification.

2.14 Scratch Wound (Migration) Assay

Transfected HUVECs were cultivated in EBM-2 medium at 37° C., 5% $CO_2$. The scratches in the cell monolayer ware generated using 100 µl tip and the cells were photographed at 0 h, 8 h and 24 h using Zeiss Axiovert 135 microscope. Subsequently, the distance between cell fronts was measured using AxioVision documentation system (Zeiss).

2.15 Proliferation Assays

To measure proliferative capacity in miRNA-modulated cells, a WST-1 (Roche, Germany) or a standard BrdU proliferation assay (Calbiochem, Germany) was applied. MiRNA transfection was performed as mentioned before. Next, medium was changed and replaced by WST-1 or BrdU reagent as detailed by the manufacturer. WST-1 and BrdU absorbances were measured at 450 nm (WST-1) and 340 nm (BrdU), respectively.

2.16 MicroRNA Target Prediction

The microRNA databases and target prediction tools miRBase (http://microrna.sangerac.uk/), PicTar (http://pictar.mdc-berlin.de/) and TargetScan (http://www.targetscan.org/index.html) were used to identify potential microRNA targets. Specifically, targets with known expression in cardiovascular tissue were screened for. The focus was on targets predicted by at least two prediction data bases and containing a miR-24-8 mer seed match in the respective 3'UTR region.

2.17 Immunofluorescence

Frozen heart sections were acetone-fixed, washed and blocked with 5% (v/v) donkey sera or MOM Mouse IgGs (for RASA1 stain) before addition of appropriate Alexa-conjugated secondary antibodies (Invitrogen). Slides were mounted in VECTASHIELD/DAPI (Linaris). Details about used antibodies are shown in Table M6.

2.18 Luciferase Reporter Assays

A luciferase reporter assay system was applied to validate potential miRNA targets. A putative 3''-UTR miRNA binding sequence was cloned into SpeI and HindIII cloning site of pMIR-REPORT vector (Ambion). Mutations in the putative miR-24 binding sites were introduced using site directed mutagenesis (Quick Change II-Site Directed Mutagenesis Kit, Stratagene). The mutations within the 3'UTRs are as follows (8-mer seed in bold, mutated nucleotides underlined): GATA2 wild-type: 5'-CAGGCTGGGCTGAGCCAAAGC-CAGAGTG-3', GATA2 mutant 5'-CAGGCTGGGCTG GTACAAAGCCAGAGTG-3'; PAK4 wild-type 5'-CCTCTCCCCCTGAGCCATTGGGGGGGTC-3', PAK4 mutant 5'-CCTCTCCCCCTGCTCCATTGGGGGGGTC-3'. The resulting construct was co-transfected with miRNAs of interest and beta-galactosidase control plasmid (Promega) into HEK293 reporter cells in 48-wells by use of Lipofectamine 2000 (Invitrogen). 0.2 µg plasmid DNA and 100 nM miRNA were applied. Cells were incubated for 24 h before measuring luciferase and β-galactosidase activity (Promega, Germany).

2.19 Viral Transduction

The original GFP-murine-GATA2 plasmid was from Novartis (Basel, Switzerland). N-terminal GFP-tagged GATA2 was subcloned in an appropriate adenoviral entry vector. Adenoviruses were generated using the Gateway system (Invitrogen) by PCR amplification of the human cDNA sequence and recombination into the pAd/CMVN5 destination vector (Invitrogen). Subsequently, 15 µg of purified recombinant adenoviral DNA were digested with PacI and precipitated with sodium acetate. 1 µg of linearised vector was transfected to HEK 293 cells (Invitrogen) using Effectene reagent (Qiagen). After three amplifications adenoviruses were purified and titered using the Adeno X Maxi purification kit and rapid titer kit (Clontech). For viral transduction experiments cells were grown to subconfluence and infected with viral particles for 4 h before changing the medium. M.o.i. was 4-40. An YFP-control virus was also applied with same m.o.i.

2.20 Chromatin Immunoprecipitation

Chromatin immunoprecipitation (ChIP) was used to detect protein-DNA interactions. First, protein G sepharose beads were blocked o/n at 4° C. HUVECs from confluent T75 flasks were first cross-linked and harvested. The pellet was lysed and sonified to yield DNA fragments from 100-1000 bp in length. Afterwards, samples were centrifuged at maximum speed to yield cleared lysates. Aliquots were separately taken to measure sonification efficiency by agarose gel analysis. To reduce non-specific background, cleared lysates were precleared on blocked Protein G Sepharose beads (GE Healthcare) twice. Samples were subjected to either immunoprecipitation with 5 µg GATA2 antibody (Santa Cruz Biotechnology, sc-267×) or control mouse IgGs (Santa Cruz Biotechnology, sc-2025) o/n at 4° C. To block non-specific background BSA and herring sperm DNA were added. One sample with cell lysis and IP dilution buffer was used as mock control. The next day GATA2/DNA cross-links were collected by incubation with Protein G beads. Beads were washed twice with dialysis buffer and four times with IP wash buffer. Finally, beads were washed twice with TE-buffer. Antibody-GATA2/DNA complexes were eluted from the beads by adding 150 µl IP elution buffer and heating at 65° C. The elution step was repeated and combined eluates were reverse cross-linked. Samples were subjected to RNA and protein degradation. Afterwards, DNA was isolated and purified with Qiagen PCR purification kit (Qiagen).

For ChIP primer-design first 2000-2500 bp upstream promoter region of candidate target genes by Ensembl Genome Browser (http://www.ensembl.org/index.html) were identified. Subsequently, the promoter region for potential GATA2 binding sites was screened by the use of ALLGEN-Promo, and appropriate primer pairs that amplify potential GATA2 binding sites were selected. Subsequent PCR analysis of chipped DNA fragments was done by mixing 2.5 µl sample, 2.5 µl 4 µM appropriate primer pairs, 10 µl HotStarTaq Mix (Qiagen) and applying the following protocol: 94° C. 10 min, [94° C. 1 min, 57° C. 30 sec, 72° C. 1 min]×33, 72° C. 10 min, 4° C. hold. Used oligonucleotide primer sequences are given in Table M7.

2.21 Zebrafish Assays

These studies as well as all other in vivo studies described herein conform to the *Guide for the Care and Use of Laboratory Animals* published by the US National Institutes of Health (NIH Publication No. 85-23, revised 1996).

Zebrafish wildtype TU and TL lines and the transgenic line TG(flk1:eGFP$^{s843}$) were kept at 28.5° C. and staged as described (Walker et al., 2007). To inhibit pigmentation, 0.003% 1-phenyl-2-thiourea was added to the embryo medium. Embryos were injected at the 1-2 cell stage with 2 nl of pre-miR-24 (25 µM) or control pre-miRs (25 µM). Injected embryos were analysed 48 hpf (hours post fertilization). Images of living embryos were acquired with Leica MZ FLIII. For confocal analyses, zebrafish embryos were fixed at 48 hpf in a 4% paraformaldehyde solution overnight and embedded in 1.5% LMW agarose. Confocal images were obtained with Leica TCS SP2 confocal laser scanning microscope. Series of sections with the optimized step size for the individual objectives were taken. The maximum projection algorithm of the Leica software was then used to calculate information sectored in different ranks to a two-dimensional projection.

2.22 Antagomir Injection

Antagomirs were designed and provided by Regulus Therapeutics (USA) and as described (Krutzfeldt et al., 2005). Sequences were: Antagomir-24: 5'-CTGTTCCTGCT-GAACTGAGCCA-chol-3' (SEQ ID NO: 3) and scrambled Antagomir: 5'-ACAAACACCAUUGUCACACUCCA-chol-3' (SEQ ID NO: 4). Antagomirs were diluted in nuclease-free water and 100 µl at concentrations of 5 mg/kg and 80 mg/kg were applied to mice via retroorbital injection.

2.23 Myocardial Infarction

Male Mice (C57BL/6, 8-10 weeks) underwent coronary artery ligation for the production of myocardial infarction (MI). Successful generation of MI after occlusion of the left ascending artery was monitored by parallel electrocardiogram (ECG; ST-elevation) measurements and impaired wall motion by echocardiography. Only mice with significant ST-elevation in the ECG analysis and impaired wall motion by echocardiography were included in the study. Briefly, mice were anesthetized, placed on a heating pad, intubated and ventilated with a mixture of oxygen and isoflurane. After left lateral thoracotomy and exposure of the heart by retractors, the left anterior descending coronary artery (LAD) was permanently ligated. Successful production of MI was checked by measurements of ST-elevation in electrocardiograms as well as impaired left ventricular wall motion by echocardiography. Animals that did not show ST-elevation and impaired left ventricular wall motion after myocardial infarction were excluded from further studies. Fourteen days after MI, additional echocardiography measurements were performed and finally hearts were excised and cut into transverse sections. From the middle ring, sections were cut and stained with appropriate antibodies (see above). Cardiac dimensions and function were analyzed by pulse-wave Doppler echocardiography.

2.24 Analysis of Capillary and Arteriolar Density

Analyses of capillary and arteriolar density were performed in transverse sections of the peri-infarct zone and remote zone from left ventricles 14 days after MI. Capillary and arteriolar densities were evaluated after fluorescent immunohistochemical staining for Pecam-1 (endothelial marker) or α-smooth muscle actin (Acta2; smooth muscle cells). Arterioles were recognized as vessels with one or more continuous layer of Acta2-positive vascular smooth muscle cells. The number of capillaries and arterioles per $mm^2$ was counted in a blinded fashion.

2.25 Determination of Apoptotic Endothelial Cells and Cardiomyocytes in Vivo

Apoptosis was quantified at 14 days after MI by terminal deoxynucleotidyltransferase (TdT)-mediated dUTP nick-end labelling (TUNEL) technique (in situ cell death detection kit Fluorescein, Roche, Germany) and combined cell-type specific stainings of either endothelial cells (Pecam1) or cardiomyocytes (Tnni3). Following treatment of slides with proteinase K (20 µg/ml, 30 min at 37° C.), TUNEL assay was performed as described by the manufacturer. Sections were additionally stained with DAPI to recognize nuclei. At least ten high power fields (400×) from the peri-infarct zone were analysed.

2.26 Determination of Infarct Size

Cardiac ring sections were stained with picrosirius red and infarct size was determined by planimetric measurement using a microscope and calculated by dividing the sum of endocardial and epicardial circumferences of infarct areas by the sum of the total endocardial and epicardial circumferences.

2.27 Matrigel Implantation and Determination of Vascularization

300 µl Matrigel™ Basement Membrane Matrix High Concentration (BD, Germany) supplemented with 600 ng/ml bFGF, 300 ng/ml VEGF and 25 U/ml Heparin were injected subcutaneously into wildtype C57BL/6 mice and harvested two weeks later. Animals were treated post implantation with Antagomir-24 or a scrambled control antagomir (5 mg/kg at day 0 and day 2) by retroorbital injection. Half of the plug were lysed in cell lysis buffer and samples were measured for haemoglobin amount with a Mouse Hemoglobin ELISA (#E-90HM, Immunology Consultants Laboratory Inc, USA). Hemoglobin amount was normalized to total protein. Additional plugs were frozen in TissueTec, sliced, stained with CD31 antibodies and investigated by fluorescence microscopy.

2.28 Statistical Analysis

Average data are presented as mean and s.e.m. unless stated different. Statistical analysis was carried out using the Stat-View (SAS Institute) package. For statistical comparison of two groups, unpaired, two-tailed Student's t-test was used; for the comparison of three or more groups, ANOVA followed by Fisher's post-test was used. Differences were considered significant when P, 0.05. In the figures, P values are indicated by one (P, 0.05), two (P, 0.01) or three (P, 0.005) asterisks.

TABLE M1

TaqMan miRNA detection assays

| miRNA | Reference |
|---|---|
| miR-21 | Assay ID 000397, Applied Biosystems, USA |
| miR-24 | Assay ID 000402, Applied Biosystems, USA |
| miR-126 | Assay ID 002228, Applied Biosystems, USA |
| miR-499 | Assay ID 001352, Applied Biosystems, USA |
| RNU6-2 | Assay ID 001093, Applied Biosystems, USA |

TABLE M2

Primers used for mRNA RT-PCR

| Gene Assignment | primer (forward, reverse) | Product size [bp] |
|---|---|---|
| Col1A1 | forward: 5'-ttgaccctaaccaaggatgc-3'<br>reverse: 5'-cacccttctgcgttgtatt-3' | 197 |
| GAPDH | forward: 5'-aactcccattcctccaccctt-3'<br>reverse: 5'-gagggcctctctcttgctct-3' | 200 |

TABLE M3

Oligonucleotides used for in situ hybridization

| Oligo-nucleotide name | Sequence (5' to 3', LNA in lowercase) | UV melting temperature (° C.) |
|---|---|---|
| 24-2 | CtGTTCCTgCTGAACtGaGcCA | 73.3 |
| 24-3 | CTGTTCcTGcTGAACTGaGCcA | 67.0 |
| 24-4 | CtGTTCcTGCtGAACTgAgCcA | 69.0 |
| 24-5 | CTGTTCCtGcTGAACtGaGcCa | 75.3 |
| 23a | GGaAAtCCCtGgCAaTGTGaT | 68.8 |
| 23b | GGTAAtCCCTGgCAAtGtGAT | 68.0 |
| 27a | GCGGaACTtAGCCACTGTGaA | 61.9 |
| 27b | GCAGaAcTtAgCcACTGTGaA | 68.0 |

TABLE M4

Used siRNAs and miRNAs siRNAs

| siRNAs | Reference |
|---|---|
| GATA2 | sc-37228, Santa Cruz Biotechnology, USA |
| PAK4 | sc-39060, Santa Cruz Biotechnology, USA |
| H2AFX | sc-62464, Santa Cruz Biotechnology, USA |
| RASA1 | sc-29467, Santa Cruz Biotechnology, USA |
| Drosha | 10 |
| scrambled siRNA control-A | sc-37007, Santa Cruz Biotechnology, USA | miRNAs

| miRNAs | Reference |
|---|---|
| miR-24 | PM10737, Applied Biosystems, USA |
| anti-miR-24 | AM10737, Applied Biosystems, USA |
| miR-22 | PM11752, Applied Biosystems, USA |
| miR-210 | PM10516, Applied Biosystems, USA |
| pre-miR. precursor molecules-negative control #2 | PM17111, Applied Biosystems, USA |

TABLE M5

Antibodies applied in this work for Western blotting

| Antibody | Reference | Immunization |
|---|---|---|
| GAPDH | ab8245, Abcam, USA | mouse |
| GATA2 | arp31855, Aviva Systems Biology, USA | rabbit |
| GFP | ab1218, Abcam, USA | mouse |
| HMOX1 | AF3776, R&D Systems, USA | goat |
| PAK4 | ab19007, Abcam, USA | rabbit |
| BAD | ab28840, Abcam, USA | rabbit |
| RASA1 | ab2922, Abcam, USA | mouse |
| SIRT1 | ab32441, Abcam, USA | rabbit |
| H2AFX | ab11175, Abcam, USA | rabbit |
| TBP | ab818, Abcam, USA | mouse |
| DROSHA | ab12286, Abcam, USA | rabbit |

TABLE M6

Antibodies applied in this work for immunofluorescence microscopy

| Antibody | Reference | Immunization |
|---|---|---|
| PECAM1 | #2388, AbD Serotec, Germany | rat |
| TNNI3 | sc-15368, Santa Cruz Biotechnology, USA | rabbit |
| GATA2 | arp31855, Aviva Systems Biology, USA | rabbit |
| PAK4 | ab19007, Abcam, USA | rabbit |
| RASA1 | ab2922, Abcam, USA | mouse |

TABLE M7

Primers used for ChIP-PCR

| Promoter region | primer (forward, reverse) | Product size [bp] |
|---|---|---|
| BMP and activin membrane-bound inhibitor (BAMBI) | forward: 5'-tctcaggttttggagggaga-3'<br>reverse: 5'-ggccgagactgacactcaat-3' | 259 |
| Endothelial cell specific molecule 1 (ESM1) | forward: 5'-caagtgatatgccagggtca-3'<br>reverse: 5'-tggttgttttgcatgaggac-3' | 136 |
| Heme oxygenase 1 (HMOX1) | forward: 5'-catcaccagacccagacaga-3'<br>reverse: 5'-aaggccgactttaagggaag-3' | 133 |
| Netrin 4 (NTN4) | forward: 5'-gagccagttattcagcaaagaaa-3'<br>reverse: 5'-atgcagaggccatgctaatc-3' | 180 |
| Sirtuin 1 (SIRT1) | forward: 5'-ggagtcacagtgtgccagaa-3'<br>reverse: 5'-ccttcctttctagcgtgagc-3' | 201 |

REFERENCES

Bartel, D. P. MicroRNAs: Genomics, biogenesis, mechanism, and function. Cell 116, 281-297, 2004

Care, A., et al. MicroRNA-133 controls cardiac hypertrophy. Nat Med 13, 613-618, 2007

Hill, J. A., et al. Cardiac Plasticity. N Engl J Med 358, 1370-80, 2008

Krutzfeldt, J., et al. Silencing of microRNAs in vivo with 'antagomirs'. Nature 438, 685-689, 2005

Thum, T., et al. MicroRNAs in the human heart: a clue to fetal gene reprogramming in heart failure. Circulation 116, 258-267, 2007

Thum, T. MicroRNA-21 contributes to myocardial disease by stimulating MAP kinase signalling in fibroblasts. Nature 456, 2008 van Rooij, E., et al. A signature pattern of stress responsive microRNAs that can evoke cardiac hypertrophy and heart failure. PNAS 103, 18255-60, 2006

Walker, M. B., et al. phospholipase C, beta 3 is required for Endothelin) regulation of pharyngeal arch patterning in zebrafish. Developmental Biology 304, 194-207, 2007

Wang, S., et al. The Endothelial-Specific MicroRNA miR-126 Governs Vascular Integrity and Angiogenesis. Developmental Cell 15, 261-71, 2008

Wang, Q., et al. MicroRNA miR-24 inhibits erythropoiesis by targeting activin type I receptor ALK4. Blood 111, 588-595, 2008.

---

The invention claimed is:

1. A method for treatment of ischemia or endothelial apoptosis, and/or for inducing angiogenesis, wherein said method comprises administering, to a subject in need of such treatment or induction, an inhibitor of microRNA-24 (miR-24), wherein said inhibitor is a nucleic acid.

2. The method, according to claim 1, wherein the ischemia is associated with at least one of the group consisting of acute and/or chronic myocardial infarction, chronic heart failure, peripheral vascular occlusive disease, liver and/or kidney ischemia, stroke, bowel ischemia and chronic ulcers of the skin and/or the mucosa.

3. The method, according to claim 1, wherein the inhibitor is an antagomir or an antisense oligonucleotide.

4. The method, according to claim 3, wherein the antagomir or the antisense oligonucleotide is essentially complementary to SEQ ID NO: 1.

* * * * *

UNITED STATES PATENT AND TRADEMARK OFFICE
CERTIFICATE OF CORRECTION

PATENT NO. : 8,691,783 B2  
APPLICATION NO. : 13/384228  
DATED : April 8, 2014  
INVENTOR(S) : Thomas Thum et al.

Page 1 of 1

It is certified that error appears in the above-identified patent and that said Letters Patent is hereby corrected as shown below:

In the Specification

Column 25,  
Line 44, "3"-UTR" should read --3'-UTR--.

Column 26,  
Line 2, "pAd/CMVN5" should read --pAd/CMV/V5--.

Column 29,  
Line 26, "siRNAs" should read --siRNA--.

Column 29,  
Line 36, "miRNAS" should read --miRNA--.

Column 32,  
Line 8, "Endothelin)" should read --Endothelin 1--.

Signed and Sealed this  
Nineteenth Day of August, 2014

Michelle K. Lee  
*Deputy Director of the United States Patent and Trademark Office*